US008686111B2

(12) United States Patent
Hartley

(10) Patent No.: US 8,686,111 B2
(45) Date of Patent: Apr. 1, 2014

(54) CYTOKINE DERIVATIVES

(75) Inventor: Oliver Hartley, Genève (CH)

(73) Assignee: Mintaka Foundation for Medical Research, Geneva (CH)

( * ) Notice: Subject to any disclaimer, the term of this patent is extended or adjusted under 35 U.S.C. 154(b) by 724 days.

(21) Appl. No.: 12/309,569

(22) PCT Filed: Jul. 25, 2007

(86) PCT No.: PCT/IB2007/003026
§ 371 (c)(1),
(2), (4) Date: Jun. 17, 2009

(87) PCT Pub. No.: WO2008/012689
PCT Pub. Date: Jan. 31, 2008

(65) Prior Publication Data
US 2009/0317363 A1 Dec. 24, 2009

(30) Foreign Application Priority Data
Jul. 25, 2006 (GB) .................................. 0614755.7

(51) Int. Cl.
*C07K 14/00* (2006.01)

(52) U.S. Cl.
USPC .......................................... 530/324; 514/3.8

(58) Field of Classification Search
USPC .......................................... 530/324; 514/3.8
See application file for complete search history.

(56) References Cited

FOREIGN PATENT DOCUMENTS

| EP | 1316801 | 6/2003 |
|---|---|---|
| WO | WO97/44462 | 11/1997 |
| WO | 02/28419 | 4/2002 |
| WO | WO03/022884 | 3/2003 |
| WO | 2005112567 | 12/2005 |

OTHER PUBLICATIONS

Watkins (Nature Medicine (Jun. 2008) vol. 14, No. 6, pp. 617-621).*
Takeuchi (Retrovirology (2012) vol. 9, 3, pp. 1-16).*
Hu Shiu-Lok (Current Drug Targets..Infectious Disorders (Jun. 2005) 5(2), 193-201).*
Van Rompay (Retrovirology (2007) vol. 4, 25, pp. 1-22).*
Wells et al., "Selectivity and antagonism of chemokine receptors", Journal of Leukocyte Biology, 1996, vol. 59, pp. 53-60.
Fernandez et al., "Structure, function and inhibition of chemokines", Annu Rev Pharmacol Toxicol, 2002, vol. 42, pp. 469-499.
Gaertner et al., "Highly potent HIV inhibition: engineering a key anti-HIV structure from PSC-RANTES into MIP-1 beta/CCL4", Protein Eng, Des Sel, 2008, vol. 21, pp. 65-72.
Hartley et al. "Human Immunodeficiency Virus Type 1 Entry Inhibitors Selected on Living Cells from a Library of Phage Chemokines", Journal of Virology, vol. 77: 6637-6644, 2003.
Polo et al. "Enhancement of the HIV-1 inhibitory activity of RANTES by modification of the N-terminal region: dissociation from CCR5 activation", Eur. J. Immunol. 30: 3190-3198, 2000.
Horuk, "Chemokine receptor antagonists: overcoming developmental hurdles", Nature Reviews Drug Discovery, 2009, vol. 8, pp. 23-33.
Lederman et al., "Microbicides and other topical strategies to prevent vaginal transmission of HIV", Nature Reviews Immunology, 2006, vol. 6, pp. 371-382.
Lederman et al., "Biology of CCR5 and its role in HIV infection and treatment", JAMA, 2006, vol. 296, No. 7, pp. 815-826.
Veazey et al., "Topically applied recombinant chemokine analogues fully protect macaques from vaginal simian-human immunodeficiency virus challenge", The Journal of Infectious Diseases, 2009, vol. 199, pp. 1525-1527.
Veazey et al., "Protection of rhesus macaques from vaginal infection by vaginally delivered maraviroc, an inhibitor of HIV-1 entry via the CCR5 co-receptor", The Journal of Infectious Diseases, 2010, vol. 202, No. 5, pp. 739-744.
Hartley et al., "Medicinal chemistry applied to a synthetic protein: development of highly potent HIV entry inhibitors", Proc Natl Acad Sci, 2004, vol. 101, No. 47, pp. 16460-16466.

* cited by examiner

*Primary Examiner* — David Lukton
(74) *Attorney, Agent, or Firm* — Klauber & Jackson LLC

(57) ABSTRACT

The invention relates to polypeptides comprising an N-terminal portion and a C-terminal portion, wherein said N-terminal portion comprises the signature sequence QGP[P or L] and the amino acid sequence of said C-terminal portion is at least 70% identical to SEQ ID NO: 1, and uses thereof.

46 Claims, 4 Drawing Sheets

SEQUENCE LISTING

```
<160> NUMBER OF SEQ ID NOS: 69

<210> SEQ ID NO 1
<211> LENGTH: 59
<212> TYPE: PRT
<213> ORGANISM: Homo sapiens

<400> SEQUENCE: 1

Cys Cys Phe Ala Tyr Ile Ala Arg Pro Leu Pro Arg Ala His Ile Lys
1               5                   10                  15

Glu Tyr Phe Tyr Thr Ser Gly Lys Cys Ser Asn Pro Ala Val Val Phe
            20                  25                  30

Val Thr Arg Lys Asn Arg Gln Val Cys Ala Asn Pro Glu Lys Lys Trp
        35                  40                  45

Val Arg Glu Tyr Ile Asn Ser Leu Glu Met Ser
    50                  55

<210> SEQ ID NO 2
<211> LENGTH: 10
<212> TYPE: PRT
<213> ORGANISM: Artificial Sequence
<220> FEATURE:
<223> OTHER INFORMATION: synthetic

<400> SEQUENCE: 2

Gln Gly Pro Pro Leu Met Ala Leu Gln Ser
1               5                   10

<210> SEQ ID NO 3
<211> LENGTH: 10
<212> TYPE: PRT
<213> ORGANISM: Artificial Sequence
<220> FEATURE:
<223> OTHER INFORMATION: synthetic

<400> SEQUENCE: 3

Gln Gly Pro Pro Leu Met Trp Met Gln Val
1               5                   10

<210> SEQ ID NO 4
<211> LENGTH: 10
<212> TYPE: PRT
<213> ORGANISM: Artificial Sequence
<220> FEATURE:
<223> OTHER INFORMATION: synthetic

<400> SEQUENCE: 4

Gln Gly Pro Pro Leu Met Trp Leu Gln Val
1               5                   10

<210> SEQ ID NO 5
<211> LENGTH: 10
<212> TYPE: PRT
```

```
<213> ORGANISM: Artificial Sequence
<220> FEATURE:
<223> OTHER INFORMATION: synthetic

<400> SEQUENCE: 5

Gln Gly Pro Pro Leu Met Trp Thr Gln Ser
1               5                   10

<210> SEQ ID NO 6
<211> LENGTH: 10
<212> TYPE: PRT
<213> ORGANISM: Artificial Sequence
<220> FEATURE:
<223> OTHER INFORMATION: synthetic

<400> SEQUENCE: 6

Gln Gly Pro Pro Leu Met Trp Leu Gln Thr
1               5                   10

<210> SEQ ID NO 7
<211> LENGTH: 10
<212> TYPE: PRT
<213> ORGANISM: Artificial Sequence
<220> FEATURE:
<223> OTHER INFORMATION: synthetic

<400> SEQUENCE: 7

Gln Gly Pro Pro Leu Met Trp Thr Gln Val
1               5                   10

<210> SEQ ID NO 8
<211> LENGTH: 10
<212> TYPE: PRT
<213> ORGANISM: Artificial Sequence
<220> FEATURE:
<223> OTHER INFORMATION: synthetic

<400> SEQUENCE: 8

Gln Gly Pro Pro Leu Met Trp Met Gln Ser
1               5                   10

<210> SEQ ID NO 9
<211> LENGTH: 10
<212> TYPE: PRT
<213> ORGANISM: Artificial Sequence
<220> FEATURE:
<223> OTHER INFORMATION: synthetic

<400> SEQUENCE: 9

Gln Gly Pro Pro Leu Met Ala Thr Gln Ser
1               5                   10

<210> SEQ ID NO 10
<211> LENGTH: 10
<212> TYPE: PRT
<213> ORGANISM: Artificial Sequence
<220> FEATURE:
<223> OTHER INFORMATION: synthetic

<400> SEQUENCE: 10

Gln Gly Pro Pro Leu Met Trp Leu Gln Ser
1               5                   10

<210> SEQ ID NO 11
<211> LENGTH: 10
<212> TYPE: PRT
<213> ORGANISM: Artificial Sequence
<220> FEATURE:
```

<223> OTHER INFORMATION: synthetic

<400> SEQUENCE: 11

Gln Gly Pro Pro Leu Met Ala Leu Gln Val
1               5                   10

<210> SEQ ID NO 12
<211> LENGTH: 10
<212> TYPE: PRT
<213> ORGANISM: Artificial Sequence
<220> FEATURE:
<223> OTHER INFORMATION: synthetic

<400> SEQUENCE: 12

Gln Gly Pro Pro Leu Met Trp Leu Gly Gly
1               5                   10

<210> SEQ ID NO 13
<211> LENGTH: 10
<212> TYPE: PRT
<213> ORGANISM: Artificial Sequence
<220> FEATURE:
<223> OTHER INFORMATION: synthetic

<400> SEQUENCE: 13

Gln Gly Pro Pro Leu Met Trp Arg Gly Ser
1               5                   10

<210> SEQ ID NO 14
<211> LENGTH: 10
<212> TYPE: PRT
<213> ORGANISM: Artificial Sequence
<220> FEATURE:
<223> OTHER INFORMATION: synthetic

<400> SEQUENCE: 14

Gln Gly Pro Leu Leu Met Trp Leu Gln Val
1               5                   10

<210> SEQ ID NO 15
<211> LENGTH: 10
<212> TYPE: PRT
<213> ORGANISM: Artificial Sequence
<220> FEATURE:
<223> OTHER INFORMATION: synthetic

<400> SEQUENCE: 15

Gln Gly Pro Pro Leu Met Gln Thr Thr Pro
1               5                   10

<210> SEQ ID NO 16
<211> LENGTH: 10
<212> TYPE: PRT
<213> ORGANISM: Artificial Sequence
<220> FEATURE:
<223> OTHER INFORMATION: synthetic

<400> SEQUENCE: 16

Gln Gly Pro Pro Gly Asp Thr Val Leu Trp
1               5                   10

<210> SEQ ID NO 17
<211> LENGTH: 10
<212> TYPE: PRT
<213> ORGANISM: Artificial Sequence
<220> FEATURE:
<223> OTHER INFORMATION: synthetic

```
<400> SEQUENCE: 17

Gln Gly Pro Pro Gly Asp Ile Val Leu Ala
1               5                   10

<210> SEQ ID NO 18
<211> LENGTH: 10
<212> TYPE: PRT
<213> ORGANISM: Artificial Sequence
<220> FEATURE:
<223> OTHER INFORMATION: synthetic

<400> SEQUENCE: 18

Gln Gly Pro Pro Gly Ser Tyr Asp Tyr Ser
1               5                   10

<210> SEQ ID NO 19
<211> LENGTH: 10
<212> TYPE: PRT
<213> ORGANISM: Artificial Sequence
<220> FEATURE:
<223> OTHER INFORMATION: synthetic

<400> SEQUENCE: 19

Gln Gly Pro Pro Gly Asp Gly Gly Ser Val
1               5                   10

<210> SEQ ID NO 20
<211> LENGTH: 10
<212> TYPE: PRT
<213> ORGANISM: Artificial Sequence
<220> FEATURE:
<223> OTHER INFORMATION: synthetic

<400> SEQUENCE: 20

Gln Gly Pro Leu Ser Gly Gln Ser Thr Pro
1               5                   10

<210> SEQ ID NO 21
<211> LENGTH: 10
<212> TYPE: PRT
<213> ORGANISM: Artificial Sequence
<220> FEATURE:
<223> OTHER INFORMATION: synthetic

<400> SEQUENCE: 21

Gln Gly Pro Pro Gly Asp Trp Leu Gln Val
1               5                   10

<210> SEQ ID NO 22
<211> LENGTH: 10
<212> TYPE: PRT
<213> ORGANISM: Artificial Sequence
<220> FEATURE:
<223> OTHER INFORMATION: synthetic

<400> SEQUENCE: 22

Gln Gly Pro Pro Leu Met Ser Phe Gln Ser
1               5                   10

<210> SEQ ID NO 23
<211> LENGTH: 10
<212> TYPE: PRT
<213> ORGANISM: Artificial Sequence
<220> FEATURE:
<223> OTHER INFORMATION: synthetic

<400> SEQUENCE: 23
```

Gln Gly Pro Pro Leu Met Ser Thr Gln Ser
1               5                   10

<210> SEQ ID NO 24
<211> LENGTH: 10
<212> TYPE: PRT
<213> ORGANISM: Artificial Sequence
<220> FEATURE:
<223> OTHER INFORMATION: synthetic

<400> SEQUENCE: 24

Gln Gly Pro Pro Leu Met Ser Leu Gln Val
1               5                   10

<210> SEQ ID NO 25
<211> LENGTH: 10
<212> TYPE: PRT
<213> ORGANISM: Artificial Sequence
<220> FEATURE:
<223> OTHER INFORMATION: synthetic

<400> SEQUENCE: 25

Gly Gly Pro Pro Leu Met Gly Leu Gln Val
1               5                   10

<210> SEQ ID NO 26
<211> LENGTH: 10
<212> TYPE: PRT
<213> ORGANISM: Artificial Sequence
<220> FEATURE:
<223> OTHER INFORMATION: synthetic

<400> SEQUENCE: 26

Gln Gly Pro Leu Ser Gly Trp Leu Gln Val
1               5                   10

<210> SEQ ID NO 27
<211> LENGTH: 10
<212> TYPE: PRT
<213> ORGANISM: Artificial Sequence
<220> FEATURE:
<223> OTHER INFORMATION: synthetic

<400> SEQUENCE: 27

Gly Gly Pro Pro Leu Met Ser Val Leu Ala
1               5                   10

<210> SEQ ID NO 28
<211> LENGTH: 10
<212> TYPE: PRT
<213> ORGANISM: Artificial Sequence
<220> FEATURE:
<223> OTHER INFORMATION: synthetic

<400> SEQUENCE: 28

Gln Gly Pro Pro Gly Ser Trp Ser Ser Val
1               5                   10

<210> SEQ ID NO 29
<211> LENGTH: 10
<212> TYPE: PRT
<213> ORGANISM: Artificial Sequence
<220> FEATURE:
<223> OTHER INFORMATION: synthetic

<400> SEQUENCE: 29

Gln Gly Pro Pro Leu Gly Ser Met Gly Pro
1               5                   10

<210> SEQ ID NO 30
<211> LENGTH: 10
<212> TYPE: PRT
<213> ORGANISM: Artificial Sequence
<220> FEATURE:
<223> OTHER INFORMATION: synthetic

<400> SEQUENCE: 30

Gln Gly Pro Pro Leu Ser Trp Leu Gln Val
1               5                   10

<210> SEQ ID NO 31
<211> LENGTH: 10
<212> TYPE: PRT
<213> ORGANISM: Artificial Sequence
<220> FEATURE:
<223> OTHER INFORMATION: synthetic

<400> SEQUENCE: 31

Gln Gly Pro Pro Leu Ser Trp Leu Gln Ser
1               5                   10

<210> SEQ ID NO 32
<211> LENGTH: 10
<212> TYPE: PRT
<213> ORGANISM: Artificial Sequence
<220> FEATURE:
<223> OTHER INFORMATION: synthetic

<400> SEQUENCE: 32

Gln Gly Pro Pro Gly Gln Trp Ser Gln Val
1               5                   10

<210> SEQ ID NO 33
<211> LENGTH: 10
<212> TYPE: PRT
<213> ORGANISM: Artificial Sequence
<220> FEATURE:
<223> OTHER INFORMATION: synthetic

<400> SEQUENCE: 33

Gln Gly Pro Pro Met Met Ala Gly Leu Ser
1               5                   10

<210> SEQ ID NO 34
<211> LENGTH: 10
<212> TYPE: PRT
<213> ORGANISM: Artificial Sequence
<220> FEATURE:
<223> OTHER INFORMATION: synthetic

<400> SEQUENCE: 34

Gln Gly Pro Pro Leu Ser Trp Gln Gln Ser
1               5                   10

<210> SEQ ID NO 35
<211> LENGTH: 10
<212> TYPE: PRT
<213> ORGANISM: Artificial Sequence
<220> FEATURE:
<223> OTHER INFORMATION: synthetic

<400> SEQUENCE: 35

Gln Gly Pro Pro Gly Met Trp Ser Gln Ser
1               5                   10

<210> SEQ ID NO 36
<211> LENGTH: 10
<212> TYPE: PRT
<213> ORGANISM: Artificial Sequence
<220> FEATURE:
<223> OTHER INFORMATION: synthetic

<400> SEQUENCE: 36

Gln Gly Pro Pro Leu Gln Trp Arg Gln Ser
1               5                   10

<210> SEQ ID NO 37
<211> LENGTH: 10
<212> TYPE: PRT
<213> ORGANISM: Artificial Sequence
<220> FEATURE:
<223> OTHER INFORMATION: synthetic

<400> SEQUENCE: 37

Gln Gly Pro Pro Leu Met Gly Thr Gln Ser
1               5                   10

<210> SEQ ID NO 38
<211> LENGTH: 10
<212> TYPE: PRT
<213> ORGANISM: Artificial Sequence
<220> FEATURE:
<223> OTHER INFORMATION: synthetic

<400> SEQUENCE: 38

Gln Gly Pro Pro Leu Met Gln Leu Gln Val
1               5                   10

<210> SEQ ID NO 39
<211> LENGTH: 10
<212> TYPE: PRT
<213> ORGANISM: Artificial Sequence
<220> FEATURE:
<223> OTHER INFORMATION: synthetic

<400> SEQUENCE: 39

Gln Gly Pro Pro Leu Ser Trp Ser Gln Val
1               5                   10

<210> SEQ ID NO 40
<211> LENGTH: 10
<212> TYPE: PRT
<213> ORGANISM: Artificial Sequence
<220> FEATURE:
<223> OTHER INFORMATION: synthetic

<400> SEQUENCE: 40

Gln Gly Pro Pro Met Ser Trp Ser Gln Ser
1               5                   10

<210> SEQ ID NO 41
<211> LENGTH: 10
<212> TYPE: PRT
<213> ORGANISM: Artificial Sequence
<220> FEATURE:
<223> OTHER INFORMATION: synthetic

<400> SEQUENCE: 41

Gln Gly Pro Pro Leu Met Asn Leu Gln Val
1               5                   10

<210> SEQ ID NO 42
<211> LENGTH: 10

```
<212> TYPE: PRT
<213> ORGANISM: Artificial Sequence
<220> FEATURE:
<223> OTHER INFORMATION: synthetic

<400> SEQUENCE: 42

Gln Gly Pro Pro Met Ser Ala Tyr Gln Val
1               5                   10

<210> SEQ ID NO 43
<211> LENGTH: 10
<212> TYPE: PRT
<213> ORGANISM: Artificial Sequence
<220> FEATURE:
<223> OTHER INFORMATION: synthetic

<400> SEQUENCE: 43

Gln Gly Pro Pro Met Gln Gly Gly Leu Ser
1               5                   10

<210> SEQ ID NO 44
<211> LENGTH: 10
<212> TYPE: PRT
<213> ORGANISM: Artificial Sequence
<220> FEATURE:
<223> OTHER INFORMATION: synthetic

<400> SEQUENCE: 44

Gln Gly Pro Pro Leu Met Ser Leu Ala Val
1               5                   10

<210> SEQ ID NO 45
<211> LENGTH: 10
<212> TYPE: PRT
<213> ORGANISM: Artificial Sequence
<220> FEATURE:
<223> OTHER INFORMATION: synthetic

<400> SEQUENCE: 45

Gln Gly Pro Pro Leu Met Ser Leu Thr Val
1               5                   10

<210> SEQ ID NO 46
<211> LENGTH: 10
<212> TYPE: PRT
<213> ORGANISM: Artificial Sequence
<220> FEATURE:
<223> OTHER INFORMATION: synthetic

<400> SEQUENCE: 46

Gln Gly Pro Leu Ser Gly Trp Ala Gln Val
1               5                   10

<210> SEQ ID NO 47
<211> LENGTH: 10
<212> TYPE: PRT
<213> ORGANISM: Artificial Sequence
<220> FEATURE:
<223> OTHER INFORMATION: synthetic

<400> SEQUENCE: 47

Gln Gly Pro Leu Ser Gln Ser Ser Gln Val
1               5                   10

<210> SEQ ID NO 48
<211> LENGTH: 10
<212> TYPE: PRT
<213> ORGANISM: Artificial Sequence
```

```
<220> FEATURE:
<223> OTHER INFORMATION: synthetic

<400> SEQUENCE: 48

Gln Gly Pro Leu Ser Ser Gln Ser Gln Val
1               5                   10

<210> SEQ ID NO 49
<211> LENGTH: 10
<212> TYPE: PRT
<213> ORGANISM: Artificial Sequence
<220> FEATURE:
<223> OTHER INFORMATION: synthetic

<400> SEQUENCE: 49

Gln Gly Pro Leu Gly Gln Gln Gly Gln Val
1               5                   10

<210> SEQ ID NO 50
<211> LENGTH: 10
<212> TYPE: PRT
<213> ORGANISM: Artificial Sequence
<220> FEATURE:
<223> OTHER INFORMATION: synthetic

<400> SEQUENCE: 50

Gln Gly Pro Pro Leu Gln Trp Phe Gln Val
1               5                   10

<210> SEQ ID NO 51
<211> LENGTH: 10
<212> TYPE: PRT
<213> ORGANISM: Artificial Sequence
<220> FEATURE:
<223> OTHER INFORMATION: synthetic

<400> SEQUENCE: 51

Gln Gly Pro Pro Leu Gln Trp Thr Gln Val
1               5                   10

<210> SEQ ID NO 52
<211> LENGTH: 10
<212> TYPE: PRT
<213> ORGANISM: Artificial Sequence
<220> FEATURE:
<223> OTHER INFORMATION: synthetic

<400> SEQUENCE: 52

Gln Gly Pro Pro Leu Met Ala Leu Ser Val
1               5                   10

<210> SEQ ID NO 53
<211> LENGTH: 10
<212> TYPE: PRT
<213> ORGANISM: Artificial Sequence
<220> FEATURE:
<223> OTHER INFORMATION: synthetic

<400> SEQUENCE: 53

Gln Gly Pro Pro Leu Met Trp Ser Gln Val
1               5                   10

<210> SEQ ID NO 54
<211> LENGTH: 10
<212> TYPE: PRT
<213> ORGANISM: Artificial Sequence
<220> FEATURE:
<223> OTHER INFORMATION: synthetic
```

```
<400> SEQUENCE: 54

Gln Gly Pro Pro Gly Gln Trp Gly Gln Val
1               5                   10

<210> SEQ ID NO 55
<211> LENGTH: 10
<212> TYPE: PRT
<213> ORGANISM: Artificial Sequence
<220> FEATURE:
<223> OTHER INFORMATION: synthetic

<400> SEQUENCE: 55

Gln Gly Pro Pro Gly Ser Trp Ser Gln Val
1               5                   10

<210> SEQ ID NO 56
<211> LENGTH: 10
<212> TYPE: PRT
<213> ORGANISM: Artificial Sequence
<220> FEATURE:
<223> OTHER INFORMATION: synthetic

<400> SEQUENCE: 56

Gln Gly Pro Pro Leu Met Ser Ser Gln Ser
1               5                   10

<210> SEQ ID NO 57
<211> LENGTH: 10
<212> TYPE: PRT
<213> ORGANISM: Artificial Sequence
<220> FEATURE:
<223> OTHER INFORMATION: synthetic

<400> SEQUENCE: 57

Gln Gly Pro Pro Leu Met Gly Leu Ser Val
1               5                   10

<210> SEQ ID NO 58
<211> LENGTH: 10
<212> TYPE: PRT
<213> ORGANISM: Artificial Sequence
<220> FEATURE:
<223> OTHER INFORMATION: synthetic

<400> SEQUENCE: 58

Gln Gly Pro Pro Leu Met Thr Leu Gln Val
1               5                   10

<210> SEQ ID NO 59
<211> LENGTH: 10
<212> TYPE: PRT
<213> ORGANISM: Artificial Sequence
<220> FEATURE:
<223> OTHER INFORMATION: synthetic

<400> SEQUENCE: 59

Gln Gly Pro Pro Gly Gln Trp Tyr Gln Ser
1               5                   10

<210> SEQ ID NO 60
<211> LENGTH: 10
<212> TYPE: PRT
<213> ORGANISM: Artificial Sequence
<220> FEATURE:
<223> OTHER INFORMATION: synthetic

<400> SEQUENCE: 60
```

-continued

Gln Gly Pro Pro Leu Gln Trp Met Gln Ala
1               5                   10

<210> SEQ ID NO 61
<211> LENGTH: 10
<212> TYPE: PRT
<213> ORGANISM: Artificial Sequence
<220> FEATURE:
<223> OTHER INFORMATION: synthetic

<400> SEQUENCE: 61

Gln Gly Pro Pro Leu Gln Trp Met Gln Val
1               5                   10

<210> SEQ ID NO 62
<211> LENGTH: 10
<212> TYPE: PRT
<213> ORGANISM: Artificial Sequence
<220> FEATURE:
<223> OTHER INFORMATION: synthetic

<400> SEQUENCE: 62

Gln Gly Pro Pro Leu Met Ser Thr Gln Val
1               5                   10

<210> SEQ ID NO 63
<211> LENGTH: 10
<212> TYPE: PRT
<213> ORGANISM: Artificial Sequence
<220> FEATURE:
<223> OTHER INFORMATION: synthetic

<400> SEQUENCE: 63

Gln Gly Pro Pro Leu Met Ser Leu Ser Val
1               5                   10

<210> SEQ ID NO 64
<211> LENGTH: 10
<212> TYPE: PRT
<213> ORGANISM: Artificial Sequence
<220> FEATURE:
<223> OTHER INFORMATION: synthetic

<400> SEQUENCE: 64

Gln Gly Pro Pro Leu Met Ser Leu Gln Ser
1               5                   10

<210> SEQ ID NO 65
<211> LENGTH: 10
<212> TYPE: PRT
<213> ORGANISM: Artificial Sequence
<220> FEATURE:
<223> OTHER INFORMATION: synthetic

<400> SEQUENCE: 65

Gln Gly Pro Pro Leu Met Ser Leu Gln Ala
1               5                   10

<210> SEQ ID NO 66
<211> LENGTH: 10
<212> TYPE: PRT
<213> ORGANISM: Artificial Sequence
<220> FEATURE:
<223> OTHER INFORMATION: synthetic

<400> SEQUENCE: 66

Gln Gly Pro Pro Leu Met Ser Val Gln Ser

```
<210> SEQ ID NO 67
<211> LENGTH: 10
<212> TYPE: PRT
<213> ORGANISM: Artificial Sequence
<220> FEATURE:
<223> OTHER INFORMATION: synthetic

<400> SEQUENCE: 67

Gln Gly Pro Pro Leu Met Ser Ala Gln Ser
1               5                   10

<210> SEQ ID NO 68
<211> LENGTH: 10
<212> TYPE: PRT
<213> ORGANISM: Artificial Sequence
<220> FEATURE:
<223> OTHER INFORMATION: synthetic

<400> SEQUENCE: 68

Gln Gly Pro Pro Leu Met Ser Gly Gln Ser
1               5                   10

<210> SEQ ID NO 69
<211> LENGTH: 10
<212> TYPE: PRT
<213> ORGANISM: Artificial Sequence
<220> FEATURE:
<223> OTHER INFORMATION: synthetic

<400> SEQUENCE: 69

Gln Gly Pro Pro Leu Met Ser Gly Gln Val
1               5                   10
```

US 8,686,111 B2

CYTOKINE DERIVATIVES

TECHNICAL FIELD

This invention relates to cytokine derivatives having anti-HIV, anti-inflammatory or other activities.

BACKGROUND OF THE INVENTION

No drug is known to be capable of curing Human Immunodeficiency Virus (HIV) infections and Acquired Immunodeficiency Syndrome (AIDS). To date, no vaccine capable of preventing infection by HIV appears within reach.

Existing HIV infections can today, in many cases, be controlled by Highly Active Antiretroviral Therapy (HAART) which involves a combination of three or more retroviral drugs. However, the occurrence of single, double or triple-drug class resistant HIV strains is constantly rising under the selective pressure from the reverse transcriptase and protease inhibitors (RTIs and PIs) currently employed in HAART.

There is therefore an urgent need for new types of anti-HIV drugs. Preferably, such new drugs would target aspects of the virus that are less vulnerable to the development of resistance than reverse transcription and viral maturation processes targeted by the above-mentioned RTIs and PIs. In the absence of an HIV vaccine, there is furthermore a need for agents that are capable of preventing transmission of HIV during sexual contact.

This need could potentially be fulfilled by agents that inhibit the entry of HIV into target cells, i.e., agents from the class of "entry inhibitors" (EI). Such agents could, for example, be locally and topically applied to the human genitals in order to prevent infection of cells by HIV during sexual contact. Agents that can prevent the transmission of HIV during sexual contact are often (though inappropriately) referred to as "microbicides".

Entry of HIV into human target cells depends upon the attachment of the HIV virion to the human cell surface protein CD4 and a so-called coreceptor. Major coreceptors used by HIV include the seven transmembrane G-protein coupled receptors CXCR4 and CCR5. Natural chemokine ligands of CCR5, in particular RANTES (CCR5), were found to inhibit entry of R5-tropic HIV strains (strains of HIV that use CCR5 as a coreceptor) into human cells [1]. RANTES is a proinflammatory cytokine that is known to promote cell accumulation and activation in chronic inflammatory diseases.

Certain derivatives of RANTES with modifications at the N terminus displayed enhanced anti-HIV activity, e.g., AOP-RANTES, the aminooxypentane oxime of [glyoxylyl]$^1$RANTES (2-68) [2] wherein "(2-68)" denotes residues 2 to 68 of the naturally occurring RANTES peptide. Further chemically modified RANTES derivatives with anti-HIV activity include NNY-RANTES (n-nonanoyl-RANTES (2-68) [3,4]) and PSC-RANTES [5].

However, the chemically modified RANTES derivatives mentioned above not only inhibit HIV entry into cells, but are also relatively strong agonists of CCR5: AOP-, NNY- and PSC-RANTES elicit a pro-inflammatory signalling cascade involving cytosolic calcium influx. The use of agents with such signalling activity as anti-HIV drugs could lead to unwanted side effects involving, e.g., inflammation. Induction of inflammation is a highly undesirable side effect for prophylactic anti-HIV agents, as it has been recognised that the risk of infection by HIV may in fact be increased in inflamed tissue.

Agents such as RANTES derivatives may also induce signalling in target cells due to lack of selectivity or specificity of the agent for CCR5, i.e. in that the agent binds also to the receptor proteins CCR1 and CCR3.

A disadvantage of chemically modified polypeptides is that they cannot be produced by straightforward biotechnological means (expression and fermentation). Fully-coded anti-HIV RANTES derivatives, i.e. derivatives consisting only of naturally encoded amino acids have also been reported [6,7]. However, the anti-HIV potency of all initially reported fully-coded RANTES derivatives was lower than that of the chemically modified variant PSC-RANTES [5].

DISCLOSURE OF THE INVENTION

Molecules of the Invention

Fully-coded peptide agents with high anti-HIV potency have now been identified. These peptide agents may easily be produced by standard biotechnological methods, avoiding the expense and effort required for chemical synthesis or modification. Unexpectedly, it has been found that, in preferred embodiments, the peptide agents of the present invention combine high anti-HIV potency with a capacity to elicit only a low degree of pro-inflammatory signalling, thus avoiding inflammatory side effects.

In further embodiments, the agents of the invention lead to the internalisation of CCR5 into the cell (receptor sequestration, down-regulation or down-modulation). This surprising mechanism of action is advantageous, as (i) protection of comparatively long duration may be achieved by a single dose of the drug, and (ii) resistant R5-tropic HIV strains are less likely to evolve if neither CCR5 nor its drug-bound form are accessible on the surface of the target cell for interaction with the virus.

Particularly preferred peptide agents combine high anti-HIV potency with both high receptor sequestration activity and low signalling activity. Further preferred peptide agents of the invention combine at least one desirable property selected from the group consisting of high anti-HIV potency, high receptor sequestration activity and low signalling activity with high receptor selectivity, i.e. preferred binding to CCR5 over CCR1 and/or CCR3.

The peptide agents of the invention comprise a signature sequence comprising QGP[P or L], i.e., the fourth position of the signature sequence may be either P or L. Preferably, this signature sequence is located near the N terminus of the polypeptide. Preferably, the signature sequence is located such that the beginning of the signature sequence lies within 15 residues of the N terminus of the polypeptide, more preferably within 12, 10, 8, 6, 5, 4, 3, 2, 1 residues of the N terminus. Herein, the expression "the beginning of the signature sequence" refers to the N terminus of the signature sequence. The signature sequence may also be located at the extreme N terminus of the polypeptide, i.e., the N termini of the polypeptide as a whole and the signature sequence may coincide.

Thus, the invention relates to a polypeptide comprising an N-terminal portion and a C-terminal portion, wherein said N-terminal portion comprises the signature sequence QGP[P or L] and the amino acid sequence of said C-terminal portion is at least 70% identical to SEQ ID NO: 1.

Preferably, said signature sequence is
QGP[P or L][L or G or S or M][M or D or S or Q or G], or in a further preferred embodiment,
QGP[P or L][L or G][M or D or S].

More preferably, said signature sequence is
QGP[P or L][L or G or S or M][M or D or S or Q or G]XX[Q or G or L or A or T or S]X, or in a further preferred embodiment,
QGP[P or L][L or G][M or D or S]XX[Q or L]X, wherein X denotes any natural or modified amino acid.

More preferably, said signature sequence is QGP[P or L]LM or QGPPG[D or S].

More preferably, said signature sequence is QGPPLM or QGPPGD.

In one embodiment, said signature sequence is
QGP[P or L][L or M][M or Q][A or W or G or Q or N]X[Q or G or L][S or V or T or G], or in further preferred embodiments, QGP[P or L][L or M]K[or Q][A or W or G or Q or N][L or T or M or S or G or Q or R or Y][Q or G or L][S or V or T or G], or QGP[P or L]LM[A or W][L or T or M][[Q or G][S or V or T or G].

Preferably, said signature sequence is QGPPLM[A or W][L or T or M][[Q or G][S or V or T or G].

In a further embodiment, said signature sequence is
QGP[P or L][L or G or S][D or S or G or Q] XX[L or A or T or Q][W or A or V], or in further preferred embodiments,
QGP[P or L][L or G or S][D or S or G or Q][T or I or S or W or Q][V or L or A or S or G][L or A or T or Q][W or A or V], or
QGPPG[D or S][T or I]VL[W or A].

Preferably, said signature sequence is QGPPGD[T or I]VL[W or A].

In a further embodiment, said signature sequence is
QGPP[G or L][M or Q]XX[Q or S][S or V], or in further preferred embodiments,
QGPP[G or L][M or Q][S or G or W or A or T][L or F or T or S or G or Y][Q or S][S or V], or
QGPPLM[S or G][L or F or T]Q[S or V].

According to preferred embodiments, the polypeptide of the present invention comprises a signature sequence selected from the group QGPPLMALQS, QGPPLMWMQV, QGPPLMWLQV, QGPPLMWTQS, QGPPLMWLQT, QGPPLMWTQV, QGPPLMWMQS, QGPPLMATQS, QGPPLMWLQS, QGPPLMALQV, QGPPLMWLGG, QGPPLMWRGS, QGPLLMWLQV, QGPPLMQTTP, QGPPLSWLQV, QGPPLSWLQS, QGPPGQWSQV, QGPPMMAGLS, QGPPLSWQQS, QGPPGMWSQS, QGPPLQWRQS, QGPPLMGTQS, QGPPLMQLQV, QGPPLSWSQV, QGPPMSWSQS, QGPPLMNLQV, QGPPMSAYQV and QGPPMQGGLS.

According to further preferred embodiments, the polypeptide of the present invention comprises a signature sequence selected from the group QGPPGDTVLW, QGPPGDIVLA, QGPPGSYDYS, QGPPGDGGSV, QGPLSGQSTP, QGPPGDWLQV, QGPPLMSLAV, QGPPLMSLTV, QGPLSGWAQV, QGPLSQSSQV, QGPLSSQSQV and QGPLGQQGQV.

According to further preferred embodiments, the polypeptide of the present invention comprises a signature sequence selected from the group QGPPLMSFQS, QGPPLMSTQS, QGPPLMSLQV, QGPPLMGLQV, QGPLSGWLQV, QGPPLQWFQV, QGPPLQWTQV, QGPPLMALSV, QGPPLMWSQV, QGPPGQWGQV, QGPPGSWSQV, QGPPLMSSQS, QGPPLMGLSV, QGPPLMTLQV and QGPPGQWYQS.

According to further preferred embodiments, the polypeptide of the present invention comprises a signature sequence selected from the group QGPPLMSVLA, QGPPGSWSSV, QGPPLGSMGP, QGPPLQWMQA, QGPPLQWMQV, QGPPLMSTQV, QGPPLMSLSV, QGPPLMSLQS, QGPPLMSLQA, QGPPLMSVQS, QGPPLMSAQS, QGPPLMSGQS and QGPPLMSGQV.

In a further embodiment, said N-terminal portion consists of no more than 15 amino acids, preferably no more than 14, 13, 12, 11, 10 amino acids. According to one preferred embodiment, said N-terminal portion consists of 10 amino acids.

According to one embodiment, the N-terminus of the C-terminal portion adjoins directly to the C-terminus of the N-terminal portion, i.e. the N-terminal portion and the C-terminal portion are directly adjoined.

In a further embodiment, said C-terminal portion of the polypeptide chain is identical to SEQ ID NO: 1.

In a further embodiment, the signature sequence is located at the extreme N terminus.

Preferred embodiments of the signature sequences of the RANTES derivatives of the present invention are set out in Table 1:

TABLE 1

| SEQ ID NO | Signature Sequence |
|---|---|
| SEQ ID NO: 2 | QGPPLMALQS |
| SEQ ID NO: 3 | QGPPLMWMQV |
| SEQ ID NO: 4 | QGPPLMWLQV |
| SEQ ID NO: 5 | QGPPLMWTQS |
| SEQ ID NO: 6 | QGPPLMWLQT |
| SEQ ID NO: 7 | QGPPLMWTQV |
| SEQ ID NO: 8 | QGPPLMWMQS |
| SEQ ID NO: 9 | QGPPLMATQS |
| SEQ ID NO: 10 | QGPPLMWLQS |
| SEQ ID NO: 11 | QGPPLMALQV |
| SEQ ID NO: 12 | QGPPLMWLGG |
| SEQ ID NO: 13 | QGPPLMWRGS |
| SEQ ID NO: 14 | QGPLLMWLQV |
| SEQ ID NO: 15 | QGPPLMQTTP |
| SEQ ID NO: 16 | QGPPGDTVLW |
| SEQ ID NO: 17 | QGPPGDIVLA |
| SEQ ID NO: 18 | QGPPGSYDYS |
| SEQ ID NO: 19 | QGPPGDGGSV |
| SEQ ID NO: 20 | QGPLSGQSTP |
| SEQ ID NO: 21 | QGPPGDWLQV |
| SEQ ID NO: 22 | QGPPLMSFQS |
| SEQ ID NO: 23 | QGPPLMSTQS |
| SEQ ID NO: 24 | QGPPLMSLQV |
| SEQ ID NO: 25 | QGPPLMGLQV |
| SEQ ID NO: 26 | QGPLSGWLQV |
| SEQ ID NO: 27 | QGPPLMSVLA |
| SEQ ID NO: 28 | QGPPGSWSSV |
| SEQ ID NO: 29 | QGPPLGSMGP |
| SEQ ID NO: 30 | QGPPLSWLQV |
| SEQ ID NO: 31 | QGPPLSWLQS |

TABLE 1-continued

| SEQ ID NO | Signature Sequence |
|---|---|
| SEQ ID NO: 32 | QGPPGQWSQV |
| SEQ ID NO: 33 | QGPPMMAGLS |
| SEQ ID NO: 34 | QGPPLSWQQS |
| SEQ ID NO: 35 | QGPPGMWSQS |
| SEQ ID NO: 36 | QGPPLQWRQS |
| SEQ ID NO: 37 | QGPPLMGTQS |
| SEQ ID NO: 38 | QGPPLMQLQV |
| SEQ ID NO: 39 | QGPPLSWSQV |
| SEQ ID NO: 40 | QGPPMSWSQS |
| SEQ ID NO: 41 | QGPPLMNLQV |
| SEQ ID NO: 42 | QGPPMSAYQV |
| SEQ ID NO: 43 | QGPPMQGGLS |
| SEQ ID NO: 44 | QGPPLMSLAV |
| SEQ ID NO: 45 | QGPPLMSLTV |
| SEQ ID NO: 46 | QGPLSGWAQV |
| SEQ ID NO: 47 | QGPLSQSSQV |
| SEQ ID NO: 48 | QGPLSSQSQV |
| SEQ ID NO: 49 | QGPLGQQGQV |
| SEQ ID NO: 50 | QGPPLQWFQV |
| SEQ ID NO: 51 | QGPPLQWTQV |
| SEQ ID NO: 52 | QGPPLMALSV |
| SEQ ID NO: 53 | QGPPLMWSQV |
| SEQ ID NO: 54 | QGPPGQWGQV |
| SEQ ID NO: 55 | QGPPGSWSQV |
| SEQ ID NO: 56 | QGPPLMSSQS |
| SEQ ID NO: 57 | QGPPLMGLSV |
| SEQ ID NO: 58 | QGPPLMTLQV |
| SEQ ID NO: 59 | QGPPGQWYQS |
| SEQ ID NO: 60 | QGPPLQWMQA |
| SEQ ID NO: 61 | QGPPLQWMQV |
| SEQ ID NO: 62 | QGPPLMSTQV |
| SEQ ID NO: 63 | QGPPLMSLSV |
| SEQ ID NO: 64 | QGPPLMSLQS |
| SEQ ID NO: 65 | QGPPLMSLQA |
| SEQ ID NO: 66 | QGPPLMSVQS |
| SEQ ID NO: 67 | QGPPLMSAQS |
| SEQ ID NO: 68 | QGPPLMSGQS |
| SEQ ID NO: 69 | QGPPLMSGQV |

The present invention provides the peptide agents as disclosed above and, moreover, nucleic acids encoding said peptide agents. Said nucleic acids may be referred to as "nucleic acids according to the present invention". In the following, the term "agent" encompasses both peptide agents of the present invention and nucleic acids encoding said peptide agents. The skilled person would know how to design or identify nucleic acids encoding said peptide agents, according to the genetic code.

The present invention thus discloses nucleic acids comprising one or more segments encoding one or more peptide agents according to the present invention. Said nucleic acid may RNA or DNA. Said nucleic acid may moreover be a vector, i.e. nucleic acids encoding the peptides of the present invention may be incorporated within a vector. Nucleic acids encoding the peptides of the present invention may moreover be incorporated into a virus. The invention thus also provides a virus that contains, within its genome, comprising one or more segments encoding one or more peptide agents according to the present invention.

Preferably, the peptide agents of the present invention are highly potent inhibitors of HIV entry into cells, i.e. have high anti-HIV potency. According the present invention, the expressions "high anti-HIV potency", "high potency" or "highly potent" are used with regard to agents or peptide agents having an IC50 value, as measured by the cell fusion and HIV replication assays described under Materials and Methods, of 1000 pM (1 nM) or lower, preferably less than 900, 800, 700, 600, 500, 400, 300, 200, 150, 140, 130, 120, 110, 100, 90, 80, 70, 60, 50, 40, 30, or 20 pM.

In the literature, the potency of agents is sometimes expressed in terms of "IC50" values obtained from a competitive binding assay, i.e., typically, with respect to competition with a labelled tracer molecule for binding to the receptor of interest. In that case, the IC50 is defined as the concentration of the agent at which 50% of the tracer is displaced from the receptor by said agent, and is sometimes also referred to as an "apparent affinity". However, for the agents of the present invention, it has been found that such apparent affinity IC50 values, obtained, e.g., with respect to native RANTES or MIP-1beta, are not always proportional to the anti-HIV potency of the molecule. It is thus preferable to use IC50 values obtained from the assays described under Material & Methods.

In preferred embodiments, the peptide agents are peptides or polypeptides that are related to the peptide RANTES. The peptide agents may comprise the sequence SEQ ID NO: 1, or a variant, homologue (orthologue, allelic variant, derivative, functional mutant) or fragment thereof. Preferably, said sequence or the variant, homologue, or fragment or thereof constitutes, or is located within, a different part of the peptide agent than the signature sequence. However, the signature sequence may also be contained within the variant or homologue SEQ ID NO: 1.

Said variants, homologues or fragments may contain sequence substitutions, insertions, deletions, additions or truncations.

According to the present invention, a sequence is said to bear similarity to, or to be a homologue of, SEQ ID NO: 1, if said sequence is more than 70% identical to SEQ ID NO: 1. Preferably, said sequence has more than 70% sequence identity to SEQ ID NO: 1, more preferably more than 75%, 80%, 85%, 90%, 95%, 98%, 99% or 99.9% sequence identity to SEQ ID NO: 1.

A sequence is also said to bear similarity to or to be a homologue of SEQ ID NO: 1, if it contains one or more conservative substitutions with respect to SEQ ID NO: 1.

Conservative substitutions are substitutions in the sequence of a peptide or polypeptide agent that do not lead to a significant loss of function of said agent, or which lead only to a small loss of function. Such a loss of function due to one or more conservative substitutions may be considered not to be significant if said loss amounts to less than 20% (preferably less than 15%, 10%, 6% or 4%) with respect to the function of the agent having the unsubstituted sequence. Conservative substitutions are often substitutions wherein an amino acid side chain is replaced by an amino acid side chain that is related, or similar in physicochemical properties, to the replaced residue. Such conservative substitutions may be made, for example, according to the Table below. Amino acids in the same block in the middle column and preferably in the same line in the right hand column may be substituted for each other:

TABLE 2

| aliphatic | Non-polar | G A P |
| | | I L V |
| | polar uncharged | C S T M |
| | | N Q |
| | polar charged | D E |
| | | K R H |
| aromatic | | H F W Y |

According to the present invention, a sequence is said to bear similarity to, or to be a homologue of, SEQ ID NO: 1, if more than 30% of residues in said sequence are identical or conservatively substituted with respect to SEQ ID NO: 1. Preferably, more than 35%, 40%, 45%, 50%, 55%, 60%, 65%, 70%, 75%, 80%, 85%, 90%, 95%, 98% or 99% of said sequence are identical or conservatively substituted with respect to SEQ ID NO: 1.

The invention further provides polypeptides comprising fragments of SEQ ID NO: 1 or said homologues thereof. The fragments should comprise at least n consecutive amino acids from the SEQ ID NO: 1 or said homologues thereof and, depending on the particular sequence, n is 5 or more (preferably more than 6, 8, 10, 12, 14, 16, 18, 20, 22, 24, 26, 28, 30, 32, 34, 36, 38, 40, 42, 44, 46, 48, 50, 52, 54, 55, 56, 57).

The peptide agents of the invention preferably have low signalling activity, i.e., their administration and/or binding to CCR5 causes only a low degree of pro-inflammatory signalling in target cells. Peptide agents with "low signalling activity" according to the present invention lead to a signalling response of 30% or less of the maximum response ($E_{max}$) elicited by PSC-RANTES, when tested at a concentration of 300 nM in the Calcium Flux signalling assay (see under Materials and Methods). Preferably, the peptide agents of the invention have signalling activities, as measured in said assay, of less than 30%, more preferably less than 26%, 22%, 20%, 18%, 16%, 14%, 12%, 10%, 8%, 6%, 4%, 2% or 1%.

The peptide agents of the invention preferably are selective for CCR5 over the receptors CCR1 and CCR3. According to the present invention, an agent that binds to CCR1 and/or CCR3 as well as CCR5 is still considered to have selectivity for CCR5 over CCR1 and CCR3 if it does not substantially activate CCR1 or CCR3. Most preferably, the agents of the present invention neither substantially bind nor substantially activate CCR1 and CCR3. In the context of the present invention, an agent is considered not to substantially bind CCR1 and/or CCR3 if the IC50 value of the agent with respect to CCR1 and/or CCR3 binding is greater than 50 nM, more preferably greater than 60, 70, 80, 90, 100, 110, 120, 130, 140, 150, 200, 300, 400, 500, 600, 700, 800, 900 or 1000 nM, as measured using the CCR1 Discrimination Binding Assay and/or the CCR3 Discrimination Binding Assay (see Materials and Methods). Selectivity of CCR5 activation over CCR1 and/or CCR3 activation may be evaluated by means of the Calcium Flux Assay as described under Materials and Methods. In the context of the present invention, an agent is considered not to substantially activate CCR1 and/or CCR3 if its signalling activity is less than 30%, more preferably less than 26%, 22%, 20%, 18%, 16%, 14%, 12%, 10%, 8%, 6%, 4%, 2% or 1% of the $E_{max}$ elicited on that receptor by native RANTES/CCL5, as measured by the Calcium Flux Assay.

The peptide agents of the invention preferably have high receptor sequestration activity, i.e. administration and/or binding to CCR5 causes a high degree of receptor sequestration. Said sequestration is preferably receptor internalisation, down-regulation or down-modulation. Peptide agents with "high receptor sequestration activity" according to the present invention lead to the sequestration of at least 50% of the control level of surface CCR5 molecules, when tested in the CCR5 Surface Downmodulation/receptor sequestration assay (see under Materials and Methods). Preferably, peptide agents of the invention have receptor sequestration activities of more than 50% of the control level of surface CCR5, e.g. at least 55%, 60%, 65%, 70%, 80%, 85%, 90%, or 95% of the control level of surface CCR5.

Preferably, the agents of the invention combine high anti-HIV potency with low signalling activity, or combine high anti-HIV potency with high receptor sequestration activity. More preferably, the agents of the invention combine high anti-HIV potency with both low signalling and high receptor sequestration activity. Moreover, the agents of the invention preferably combine at least one property selected from the group consisting of high anti-HIV potency, high receptor sequestration activity and low signalling activity with selectivity for CCR5. According to certain preferred embodiments of the invention, the agents of the invention are characterised by a combination of intermediate levels of anti-HIV potency (IC50 levels, as measured by the Cell Fusion Assay, of e.g., between 0.15 and 1 nM, between 0.15 and 0.7 nM, between 0.3 and 1 nM or between 0.5 and 1 nM) with intermediate levels of signalling activity (e.g., between 30% and 50%, or between 30% and 45% as measured by the Calcium Flux Assay) and intermediate levels of receptor sequestration activity (e.g., between 20% and 60%, between 30% and 50%, between 20% and 50%, or between 30% and 60%, as measured by the CCR5 Surface Downmodulation Assay. Assays are described below, under Materials and Methods.

The terms protein, "peptide" or "polypeptide" are used interchangeably and refer to amino acid polymers of any length. The polymer may be linear or branched, it may comprise modified amino acids, and it may be interrupted by non-amino acids. The terms also encompass an amino acid polymer that has been modified naturally or by intervention; for example, disulfide bond formation, glycosylation, lipidation, acetylation, phosphorylation, or any other manipulation or modification, such as conjugation with a labelling component. Also included within the definition are, for example, polypeptides containing one or more analogues of an amino acid (including, for example, unnatural amino acids, etc.), as well as other modifications known in the art. Polypeptides can occur as single chains or associated chains. Polypeptides of the invention can be naturally or non-naturally glycosylated (i.e. the polypeptide has a glycosylation pattern that differs from the glycosylation pattern found in the corresponding naturally occurring polypeptide).

Preparation of the Peptide Agents

Peptide agents of the invention can be prepared in many ways, for example, using known techniques of molecular biology (i.e. genetic engineering and fermentation—in general, biotechnology) or protein chemistry (for example, chemical peptide synthesis).

The peptide and nucleic acid agents are preferably prepared using the known techniques of genetic engineering as described, for example, in [13]. The invention thus provides a process for producing peptide agents or polypeptides of the invention, comprising the step of culturing a host cell under conditions which induce polypeptide expression.

For example, peptide agents of the present invention may be prepared in recombinant form by expression in a host cell. Such expression methods are well known to those of skill in the art and many are described in detail in [13]. A suitable expression vector can be chosen for the host of choice. The vector may contain a recombinant DNA molecule encoding a peptide agent operatively linked to an expression control sequence that is recognised by the host transcription machinery. When a peptide agent of the invention is thus produced by recombinant expression, the agent is recovered by purification from a culture of host cells.

A preferred method involves in vitro chemical synthesis [8,9]. The invention thus provides a process for producing a peptide agent, wherein the peptide agent is synthesised in part or in whole using chemical means. Solid-phase peptide synthesis is particularly preferred, such as methods based on tBoc or Fmoc [10] chemistry. Enzymatic synthesis [11] may also be used in part or in full.

Biological synthesis other than by expression in a host cell may be used, e.g. the polypeptides may be produced by translation from RNA in vitro. Peptide agents of the invention can, for example, also be prepared by digesting longer polypeptides using proteases.

Biological methods, including genetic engineering, fermentation, and expression, are in general restricted to the production of polypeptides based on L-amino acids, but manipulation of translation machinery in vivo or in vitro (e.g. of aminoacyl tRNA molecules) can be used to allow the introduction of D-amino acids (or of other non natural amino acids, such as iodotyrosine or methylphenylalanine, azidohomoalanine, etc.) [12]. Where D-amino acids are included, however, it is preferred to use chemical synthesis. Polypeptides of the invention may have covalent modifications at the C-terminus and/or N-terminus.

Host Cells

The present invention also provides a host cell comprising a nucleic acid according the present invention.

According to one aspect of the invention, the host cell is suitable for biotechnological production of the agents of the present invention. Suitable hosts for biotechnological production of the agents of the present invention include commonly used prokaryotic species, such as *E. coli*, or eukaryotic yeasts that can be made to express high levels of recombinant proteins and that can easily be grown in large quantities. Cell lines grown in vitro are also suitable, particularly when using virus-driven expression systems such as the Baculovirus expression system which involves the use of insect cells as hosts. Peptide agents may also be expressed in vivo, for example in insect larvae or in mammalian tissues. Preferably, the peptide agent is expressed in *E. coli*; for example, strain BLR(DE3) is suitable, although equivalent systems are equally appropriate, as the skilled reader will be aware.

According to a further aspect of the invention, a host cell is provided that is capable of surviving and being propagated in the human or animal intestine (gut) or vagina, and preferably of expressing therein the peptide agent encoded by said nucleic acid. Preferably, the host cell according to this aspect of the invention also secretes said peptide agent into the periplasm or medium. Hereinafter, the term "agent" furthermore comprises host cells as described herein.

Preferably, the host cell is a highly colonising and non-pathogenic micro-organism. Highly colonising micro-organisms according to the present invention are strains that are capable of competing with indigenous microbes for prolonged colonisation of internal mucosal surfaces. The host cell is preferably a micro-organism that belongs to the flora of the human gut or vagina, more preferably a micro-organism that is commonly found in the flora of the human gut or vagina. More preferably, the host cell is a probiotic and/or commensal micro-organism, i.e., a genus, species or strain that is beneficial at least to the human host. Preferably host cell according to the present invention is part of the normal or healthy human or animal intestinal or vaginal flora. According to one embodiment, the host cell belongs to a genus selected from the group consisting of *Bacteroides, Clostridium, Fusobacterium, Eubacterium, Ruminococcus, Peptococcus, Peptostreptococcus, Bifidobacterium, Streptococcus, Escherichia* and *Lactobacillus*. The host cell is preferably a species selected from the group consisting of *Escherichia coli, Lactobacillus acidophilus, Lactobacillus crispatus, Lactobacillus gasseri, Lactobacillus iners, Lactobacillus jensenii, Lactobacillus casei, Lactobacillus plantarum, Lactobacillus rhammosus, Lactobacillus GG, Bifidobacterium bifidum, Bifidobacterium breve, Bifidobacterium infantis, Bifidobacterium longum* and *Streptococcus gordonii*. Preferably, the highly colonising micro-organism according to the present invention is *Escherichia coli* Nissle 1917. However, any other highly colonising strain of either *Escherichia coli* or another of the aforementioned species is also preferred strain according to the present invention. In another embodiment, the host cell is a yeast. Preferably, the yeast is a commensal yeast such as *Pichia guelliermondii* or *Saccharomyces boulardii*. In yet another embodiment, the host cell is a human cell.

The skilled person is well acquainted with methods of transforming micro-organisms with foreign nucleic acids and subsequently using the transformed micro-organisms to express a polypeptide encoded by said nucleic acids, in intracellular, periplasmic or secreted form [see references 13, 15, 16, 17].

Pharmaceutical Compositions

The present invention provides compositions comprising an agent according to the present invention and a pharmaceutically acceptable carrier. The agents of the present invention, or a pharmaceutically acceptable salt of the peptide agents or corresponding nucleic acids, are thus provided for use as a medicament. Compositions according to the present invention may comprise any agent of the present invention, i.e., hereinafter, a peptide agent, a pharmaceutically acceptable salt thereof, a nucleic acid, a pharmaceutically acceptable salt thereof, or a host cell according to the present invention. The preparation of pharmaceutical compositions is well known to the person skilled in the art.

The pharmaceutical compositions of the present invention may, in particular, comprise more than one agent (multiple) of the present invention, e.g., two or more agents. The invention also provides a pharmaceutical preparation or system, comprising (a) a first agent, which is an agent of the invention; and (b) a second pharmaceutical agent. According to certain embodiments, the second pharmaceutical agent may include reverse transcriptase inhibitors (RTI), protease inhibitors (PI), integrase inhibitors and viral assembly inhibitors. According to further embodiments, the second pharmaceutical agent may include other entry inhibitors than those of the present invention, for example, polyanionic substances (e.g., cellulose sulphate), glycan binding agents or lectins, glycan receptor binders (e.g., soluble mannan), antibodies, small-molecule entry inhibitors, peptide entry inhibitors, or CXCR4-binding (CXCR4-blocking) agents. According to yet further embodiments, the second pharmaceutical agent may include a detergent, or an agent that modifies pH, for example an acid or a pH buffering agent. According to yet further embodiments, the second pharmaceutical agent may include an inhibitory RNA (siRNA), wherein the siRNA may be chemically modified.

According to other aspects of the invention, said second agent may also be an anti-inflammatory drug or an immunosuppressant. Said multiple agents of the invention or said first and second agents are formulated either in admixture or as separate compositions, e.g. for simultaneous though separate, or for sequential administration (see below).

Pharmaceutically acceptable salts of the agents of the invention can of course be made by conventional procedures, such as by reacting the free base and/or acid of the agent with at least a stoichiometric amount of the desired salt-forming acid or base.

Pharmaceutically acceptable salts of agents of the invention include salts with inorganic cations such as sodium, potassium, calcium, magnesium, zinc, and ammonium, and salts with organic bases. Suitable organic bases include N-methyl-D-glucamine, arginine, benzathine, diolamine, olamine, procaine and troniethamine. Pharmaceutically acceptable salts of the agents of the invention also include salts derived from organic or inorganic acids. Suitable anions include acetate, adipate, besylate, bromide, camsylate, chloride, citrate, edisylate, estolate, fumarate, gluceptate, gluconate, glucuronate, hippurate, hyclate, hydrobromide, hydrochloride, iodide, isethionate, lactate, lactobionate, maleate, mesylate, methylbromide, methylsulfate, napsylate, nitrate, oleate, pamoate, phosphate, polygalacturonate, stearate, succinate, sulfate, sulfosalicylate, tannate, tartrate, terephthalate, tosylate and triethiodide.

Pharmaceutical dosage forms of an agent of the invention may be provided in an instant release, controlled release, sustained release, or target drug-delivery system.

Commonly used dosage forms include, for example, solutions and suspensions, (micro-) emulsions, ointments, gels, creams, pastes, foams, suppositories, ovules, implants, patches, liposomes, tablets, dragees, lozenges, soft or hard shell capsules, amorphous or crystalline powders, effervescent powders or tablets, aerosols, and lyophilized formulations. Depending on the route of administration used, special devices may be required for application or administration of the drug, such as, for example, syringes and needles, inhalers, pumps, injection pens, applicators, special flasks, or other devices for administration, which may also be implanted within the body. In particular, the agents of the present invention may, for example, also be comprised within, or associated with, a contraceptive device or agent, for example, an intrauterine or intracervical device, coil or diaphragm, or distributed on a condom, e.g., contained in form of a coating liquid, solution, gel or powder. However, according to the present invention, the agents of the present invention need not necessarily be associated with a contraceptive device or agent. Preferably, agent of the invention is comprised within and administered by a depot delivery system. Preferably, said depot delivery system comprises a vaginal ring or other implant that is suitable for insertion and/or implantation into the vagina or cervix and provides slow (controlled and/or sustained) release of the agent of the present invention.

Pharmaceutical dosage forms are often composed of the drug, an excipient(s), and a container/closure system. One or multiple excipients, also referred to as inactive ingredients, can be added to an agent of the invention to improve or facilitate manufacturing, stability, administration, and safety of the drug, and can provide a means to achieve a desired drug release profile. Therefore, the type of excipient(s) to be added to the drug can depend on various factors, such as, for example, the physical and chemical properties of the drug, the route of administration, and the manufacturing procedure. Pharmaceutically acceptable excipients are available in the art, and include those listed in various pharmacopoeias. (See, e.g., [18, 19])

Pharmaceutical dosage forms of an agent of the present invention may be manufactured by any of the methods well-known in the art, such as, for example, by conventional mixing, sieving, dissolving, melting, granulating, dragee-making, tabletting, suspending, extruding, spray-drying, levigating, emulsifying, (nano/micro-) encapsulating, entrapping, or lyophilization processes. As noted above, the compositions of the present invention can include one or more physiologically acceptable inactive ingredients that facilitate processing of active molecules into preparations for pharmaceutical use.

Proper formulation is dependent upon the desired route of administration. For intravenous injection, for example, the composition may be formulated in aqueous solution, if necessary using physiologically compatible buffers, including, for example, phosphate, histidine, or citrate for adjustment of the formulation pH, and a tonicity agent, such as, for example, sodium chloride or dextrose. For transmucosal or nasal administration, semisolid, liquid formulations, or patches may be preferred, possibly containing penetration enhancers. Such penetrants are generally known in the art. For oral administration, the agents can be formulated in liquid or solid dosage forms and as instant or controlled/sustained release formulations. Suitable dosage forms for oral ingestion by a subject include tablets, pills, dragees, hard and soft shell capsules, liquids, gels, syrups, slurries, suspensions, and emulsions. The agents may also be formulated in rectal compositions, such as suppositories or retention enemas, e.g., containing conventional suppository bases such as cocoa butter or other glycerides. For vaginal suppositories, many different suppository bases known to the skilled person may be used, e.g., glycerinated gelatin, depolarized gelatin, cocoa butter, polyethylene glycol, polysorbate, or others.

For oral administration, the agents of the invention will generally be provided in solid dosage forms, e.g., in the form of tablets or capsules, or as an aqueous solution or suspension.

Solid oral dosage forms can be obtained using excipients, which may include inert diluents, fillers, disintegrants, binders (dry and wet), dissolution retardants, lubricants, glidants, antiadherants, cationic exchange resins, wetting agents, antioxidants, preservatives, colouring, sweetening and flavouring agents. These excipients can be of synthetic or natural source. Examples of such excipients include cellulose derivatives, citric acid, dicalcium phosphate, gelatine, magnesium carbonate, magnesium/sodium lauryl sulfate, mannitol, polyethylene glycol, polyvinyl pyrrolidone, silicates, silicium dioxide, sodium benzoate, sorbitol, starches, stearic acid or a salt thereof, sugars (i.e. dextrose, sucrose, lactose, etc.), talc, tragacanth mucilage, vegetable oils (hydrogenated), and waxes. Ethanol and water may serve as granulation aides. In certain instances, coating of tablets with, for example, a taste-masking film, a stomach acid resistant film, or a release-retarding film is desirable. Natural and synthetic polymers, in combination with colorants, sugars, and organic solvents or water, are often used to coat tablets, resulting in dragees.

When a capsule is preferred over a tablet, the drug powder, suspension, or solution thereof can be delivered in a compatible hard or soft shell capsule.

Suitable inert diluents include sodium and calcium carbonate, sodium and calcium phosphate and lactose. Corn starch and alginic acid are suitable disintegrating agents. Binding agents may include starch and gelatine. The lubricating agent, if present, will generally be magnesium stearate, stearic acid or talc. If desired, the tablets may be coated with a material such as glyceryl monostearate or glyceryl distearate, to delay absorption in the gastrointestinal tract.

Capsules for oral use include hard gelatine capsules in which the active ingredient is mixed with a solid diluent and soft gelatine capsules wherein the active ingredient is mixed with water or an oil such as peanut oil, liquid paraffin or olive oil.

In one embodiment, the agents of the present invention can be administered topically, via the skin or mucous membrane, such as through a skin patch, a semi-solid or a liquid formulation, for example a gel, a (micro-) emulsion, an ointment, a solution, a (nano/micro)-suspension, or a foam. The penetration of the drug into the skin or mucous membrane and underlying tissues can be regulated, for example, using penetration enhancers; the appropriate choice and combination of lipophilic, hydrophilic, and amphiphilic excipients, including water, organic solvents, waxes, oils, synthetic and natural polymers, surfactants, emulsifiers; by pH adjustment; and use of complexing agents. Other techniques, such as iontophoresis, may be used to regulate skin penetration of an agent of the invention. Transdermal or topical administration would be preferred, for example, in situations in which local delivery with minimal systemic exposure is desired.

For administration by inhalation, or administration to the nose, the agents for use according to the present invention are conveniently delivered in the form of a solution, suspension, emulsion, or semisolid aerosol from pressurized packs, or a nebuliser, usually with the use of a propellant, e.g., halogenated carbons derived from methane and ethane, carbon dioxide, or any other suitable gas. For topical aerosols, hydrocarbons like butane, isobutene, and pentane are useful. In the case of a pressurized aerosol, the appropriate dosage unit may be determined by providing a valve to deliver a metered amount. Capsules and cartridges of, for example, gelatin, for use in an inhaler or insufflator, may be formulated. These typically contain a powder mix of the agent and a suitable powder base such as lactose or starch.

Compositions formulated for parenteral administration by injection are usually sterile and, can be presented in unit dosage forms, e.g., in ampoules, syringes, injection pens, or in multi-dose containers, the latter usually containing a preservative. The compositions may take such forms as suspensions, solutions, or emulsions in oily or aqueous vehicles, and may contain formulatory agents, such as buffers, tonicity agents, viscosity enhancing agents, surfactants, suspending and dispersing agents, antioxidants, biocompatible polymers, chelating agents, and preservatives. Depending on the injection site, the vehicle may contain water, a synthetic or vegetable oil, and/or organic co-solvents. In certain instances, such as with a lyophilized product or a concentrate, the parenteral formulation would be reconstituted or diluted prior to administration. Depot formulations, providing controlled or sustained release of an agent of the invention, may include injectable suspensions of nano/micro particles or nano/micro or non-micronized crystals. Polymers such as poly(lactic acid), poly(glycolic acid), or copolymers thereof, can serve as controlled/sustained release matrices, in addition to others well known in the art. Other depot delivery systems may be presented in form of implants and pumps requiring incision.

Suitable carriers for intravenous injection for the molecules of the invention are well-known in the art and include water-based solutions containing a base, such as, for example, sodium hydroxide, to form an ionized agent, sucrose or sodium chloride as a tonicity agent, for example. The water-based solution may comprise a buffer containing phosphate or histidine. Co-solvents, such as, for example, polyethylene glycols, may be added. These water-based systems are effective at dissolving agents of the invention and produce low toxicity upon systemic administration. The proportions of the components of a solution system may be varied considerably, without destroying solubility and toxicity characteristics. Furthermore, the identity of the components may be varied. For example, low-toxicity surfactants, such as polysorbates or poloxamers, may be used, as can polyethylene glycol or other co-solvents, biocompatible polymers such as polyvinyl pyrrolidone may be added, and other sugars and polyols may substitute for dextrose.

Further Aspects of the Invention

The present invention furthermore provides a kit, for example a diagnostic kit, comprising one or more peptide agents, nucleic acids or host cells according to the invention.

Uses of the Molecules of the Invention

Uses Based Upon Biological Function; Treatment and Prevention of Diseases

The present invention provides the use of the peptide agents of the present invention for blocking and/or causing the sequestration of CCR5. Sequestration may be in the form of internalisation of CCR5 into target cells and/or the down-regulation (down-modulation) of CCR5 in target cells. The invention also provides the use of nucleic acids encoding said peptide agents, or of a host cell according to the present invention (see above comprising a nucleic acid of the present invention, for the expression and optionally the secretion of said peptide agents.

As mentioned above, with regard to the present invention, the term "agent" encompasses peptide agents, nucleic acids encoding said peptide agents and host cells according to the invention. The invention provides the use of said agents for the treatment and/or prophylaxis (prevention) of diseases that may be treated by blocking and/or causing the sequestration of CCR5. The agents of the present invention are thus provided for use as medicaments.

One or more of the agents of the present invention may be administered to a subject. When more than one agent is administered, said agents may be administered together (as an admixture or separately though substantially simultaneously) or sequentially. Said one or more agents of the present invention may be administered in combination with one or more other pharmaceutically active agents that are not comprised within the agents of the present invention. The agent or agents of the present invention may then also be administered together (as an admixture or separately though substantially simultaneously) with said one or more other pharmaceutically active agents, or sequentially.

According to a preferred aspect, the present invention provides the use of said peptide agents, or of nucleic acids encoding the peptide agents, for the treatment and/or prevention of HIV infections and/or the outbreak of acquired immunodeficiency syndrome (AIDS), and/or disorders and diseases associated therewith, in a subject.

The present invention thus provides a method of treating or preventing HIV infection (the transmission of HIV) in a subject comprising the administration of a composition comprising an agent of the present invention. Furthermore, a method is provided of treating, or preventing the outbreak of, acquired immunodeficiency syndrome (AIDS) in a subject comprising the administration of a comprising an agent of the present invention.

For example, transmission of HIV, i.e. the infection of target cells by HIV, may be prevented by application of a composition according to the invention (e.g., a suppository, cream, gel, foam, paste, solution, liquid or powder containing an agent according to the present invention). In this embodiment, said composition is preferably applied to human genitals (vagina, rectum, intestine) before or during or after sexual contact in order to prevent transmission of HIV during sexual contact. Most preferably, said composition is applied before sexual contact.

The present invention also provides the use of agents of the present invention as anti-inflammatory agents. The agents are thus useful for the treatment and/or prevention of inflammatory diseases and autoimmune diseases. According to a further aspect of the invention, the agents of the present invention are useful for the treatment and/or prevention of malignant diseases and also for the treatment and/or prevention of bacterial and viral infections. Herein, the virus may be HIV or a virus other than HIV.

According to further aspects of the invention, there is also provided a method of treating or preventing inflammation, inflammatory diseases, autoimmune diseases, or bacterial and viral infections comprising the administration of a composition comprising an agent of the present invention. In particular, for example, a method is provided of treating or preventing inflammatory bowel disease, rheumatoid arthritis, atheroma or arteriosclerosis, asthma, allergic rhinitis or atopic dermatitis, the rejection of transplanted organs, tissues or cells, multiple sclerosis and/or other demyelinating diseases, peripheral neuropathy, as well as cancers, including metastasising cancers.

In one preferred embodiment of the invention, for any of the above diseases and conditions, a method of treatment or prophylaxis is provided, wherein a host cell as disclosed above is administered to a subject, said host cell expressing and secreting a peptide agent according to the present invention.

The invention also provides the use of nucleic acids of the present invention for gene therapy, wherein said nucleic acids are incorporated into a virus for administration to a subject.

Modes of Administration

The compositions of the present invention can be delivered directly or in pharmaceutical compositions containing excipients (see above), as is well known in the art. The present methods of treatment involve administration of a therapeutically effective amount of an agent of the present invention to a subject.

The term "therapeutically effective amount" as used herein refers to an amount of an agent according to the present invention needed to treat, ameliorate, or prevent the targeted disease condition, or to exhibit a detectable therapeutic or preventative effect. In general, the therapeutically effective dose can be estimated initially either in cell culture assays or in animal models, for example, in non-human primates, mice, rabbits, dogs, or pigs. The animal model may also be used to determine the appropriate concentration range and route of administration. Such information can then be used to determine useful doses and routes for administration in humans.

The precise effective amount for a human subject will depend upon the severity of the disease state, general health of the subject, age, weight, and gender of the subject, diet, time and frequency of administration, drug combination(s), reaction sensitivities, and tolerance/response to therapy. This amount can be determined by routine experimentation and is within the judgement of the clinician. Generally, an effective amount, i.e., dose, of an agent, will be from 0.005 mg/kg to 50 mg/kg, preferably 0.125 mg/kg to 20 mg/kg.

Effective treatment regimes for preferred agents of the invention include administration one, two or three times daily, and/or one, two, three, four, five or six times weekly). These regimes are therefore particularly preferred for use in the present invention.

An effective and convenient route of administration and an appropriate formulation of the agents of the invention in pharmaceutical compositions (see above) may also be readily determined by routine experimentation. Various formulations and drug delivery systems are available in the art (see, e.g., [20, 21]).

Suitable routes of administration may, for example, include vaginal, rectal, intestinal, oral, nasal (intranasal), pulmonary or other mucosal, topical, transdermal, ocular, aural, and parenteral administration.

Primary routes for parenteral administration include intravenous, intramuscular, and subcutaneous administration. Secondary routes of administration include intraperitoneal, intra-arterial, intra-articular, intracardiac, intracisternal, intradermal, intralesional, intraocular, intrapleural, intrathecal, intrauterine, and intraventricular administration. The indication to be treated, along with the physical, chemical, and biological properties of the drug, dictate the type of formulation and the route of administration to be used, as well as whether local or systemic delivery would be preferred.

For compositions useful for the present methods of treatment, a therapeutically effective dose can be estimated initially using a variety of techniques well-known in the art. Initial doses used in animal studies may be based on effective concentrations established in cell culture assays. Dosage ranges appropriate for human subjects can be determined, for example, using data obtained from animal studies and cell culture assays.

A therapeutically effective dose or amount of an agent, agent, or drug of the present invention refers to an amount or dose of the agent, agent, or drug that results in amelioration of symptoms or a prolongation of survival in a subject. Toxicity and therapeutic efficacy of such molecules can be determined by standard pharmaceutical procedures in cell cultures or experimental animals, e.g., by determining the LD50 (the dose lethal to 50% of the population) and the ED50 (the dose therapeutically effective in 50% of the population). The dose ratio of toxic to therapeutic effects is the therapeutic index, which can be expressed as the ratio LD50/ED50. Agents that exhibit high therapeutic indices are preferred.

The effective amount or therapeutically effective amount is the amount of the agent or pharmaceutical composition that will elicit the biological or medical response of a tissue, system, animal, or human that is being sought by the researcher, veterinarian, medical doctor, or other clinician, e.g., regulation of glucose metabolism, decrease in elevated or increased blood glucose levels, treatment or prevention of a disorder associated with altered glucose metabolism, e.g., diabetes, etc Dosages preferably fall within a range of circulating concentrations that includes the ED50 with little or no toxicity. Dosages may vary within this range depending upon the dosage form employed and/or the route of administration utilised. The exact formulation, route of administration, dosage, and dosage interval should be chosen according to methods known in the art, in view of the specifics of a subject's condition.

Dosage amount and interval may be adjusted individually to provide plasma levels of the active moiety that are sufficient to achieve the desired effects, i.e., minimal effective concentration (MEC). The MEC will vary for each agent but can be estimated from, for example, in vitro data and animal experiments. Dosages necessary to achieve the MEC will depend on individual characteristics and route of administration. In cases of local administration or selective uptake, the effective local concentration of the drug may not be related to plasma concentration.

The amount of agent or composition administered may be dependent on a variety of factors, including the sex, age, and weight of the subject being treated, the severity of the affliction, the manner of administration, and the judgement of the prescribing physician.

The present compositions may, if desired, be presented in a pack or dispenser device containing one or more unit dosage forms containing the active ingredient. Such a pack or device may, for example, comprise metal or plastic foil, such as a blister pack, or glass and rubber stoppers such as in vials. The pack or dispenser device may be accompanied by instructions for administration. Compositions comprising an agent of the invention formulated in a compatible pharmaceutical carrier may also be prepared, placed in an appropriate container, and labelled for treatment of an indicated condition.

The present invention thus provides a peptide agent, nucleic acid or host cell according to the invention for use in treating or preventing HIV infections, in treating and/or preventing acquired immunodeficiency syndrome (AIDS), in treating and/or preventing HIV transmission, and/or in the prevention of HIV transmission during sexual contact.

The present invention thus provides a peptide agent, nucleic acid or host cell according to the invention for use in treating and/or preventing inflammation, inflammatory diseases, autoimmune diseases, bacterial and viral infections, inflammatory bowel disease, rheumatoid arthritis, atheroma or arteriosclerosis, asthma, allergic rhinitis or atopic dermatitis, the rejection of transplanted organs, tissues or cells, multiple sclerosis and/or other demyelinating diseases, peripheral neuropathy, malignant diseases, cancers or metastasising cancers.

The present invention thus provides the use of a peptide agent, nucleic acid or host cell according to the invention for the manufacture of a medicament for treating and/or preventing HIV infections, for treating and/or preventing acquired immunodeficiency syndrome (AIDS), or the outbreak thereof, and preventing the transmission of HIV, for example during sexual contact.

The present invention provides the use of a peptide agent, nucleic acid or host cell according to the invention for the manufacture of a medicament for treating and/or preventing inflammation, inflammatory diseases, autoimmune diseases, or bacterial and viral infections, rheumatoid arthritis, atheroma or arteriosclerosis, asthma, allergic rhinitis or atopic dermatitis, the rejection of transplanted organs, tissues or cells, multiple sclerosis and/or other demyelinating diseases, peripheral neuropathy, malignant diseases, cancers or metastasising cancers.

MODES FOR CARRYING OUT THE INVENTION

Materials and Methods

Preparation of Polypeptides by Chemical Synthesis

Figure 1A:
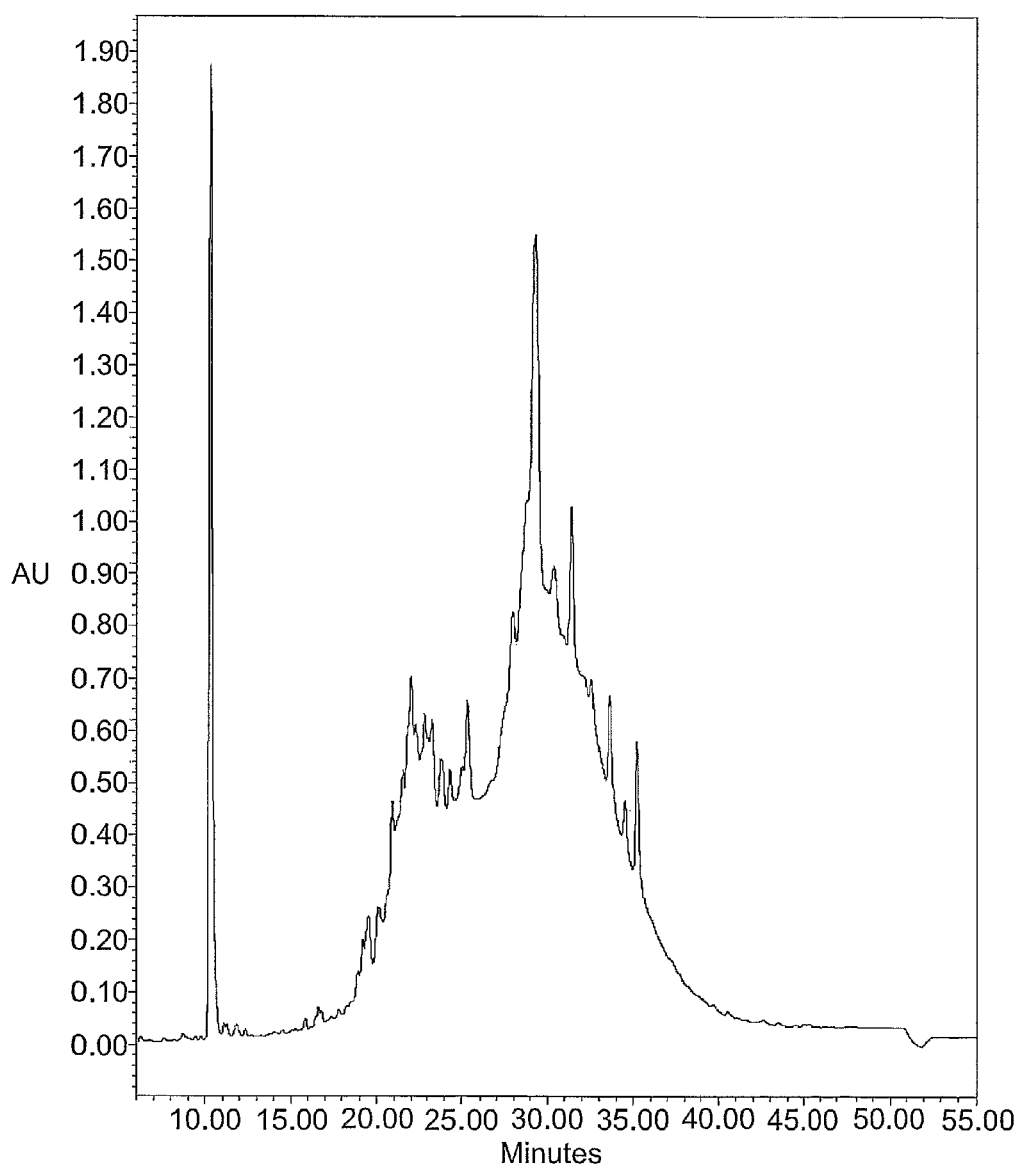
FIG. 1 shows details of the characterisation of a typical polypeptide cytokine derivative, consisting of SEQ ID NO: 21 fused to the N terminus of SEQ ID NO: 1. The polypeptide was prepared by total chemical synthesis as described in under Materials and Methods. AU: Absorption Units. Panel A shows analytical HPLC of crude material after HF cleavage. Panel B shows an analytical HPLC of desired material purified from crude preparation. Panel C shows the trace of an analytical HPLC of the reaction mixture after purification and refolding/formation of disulphide bridges. Panel D shows the trace obtained by analytical HPLC with the purified, refolded material.
Figure 1B:
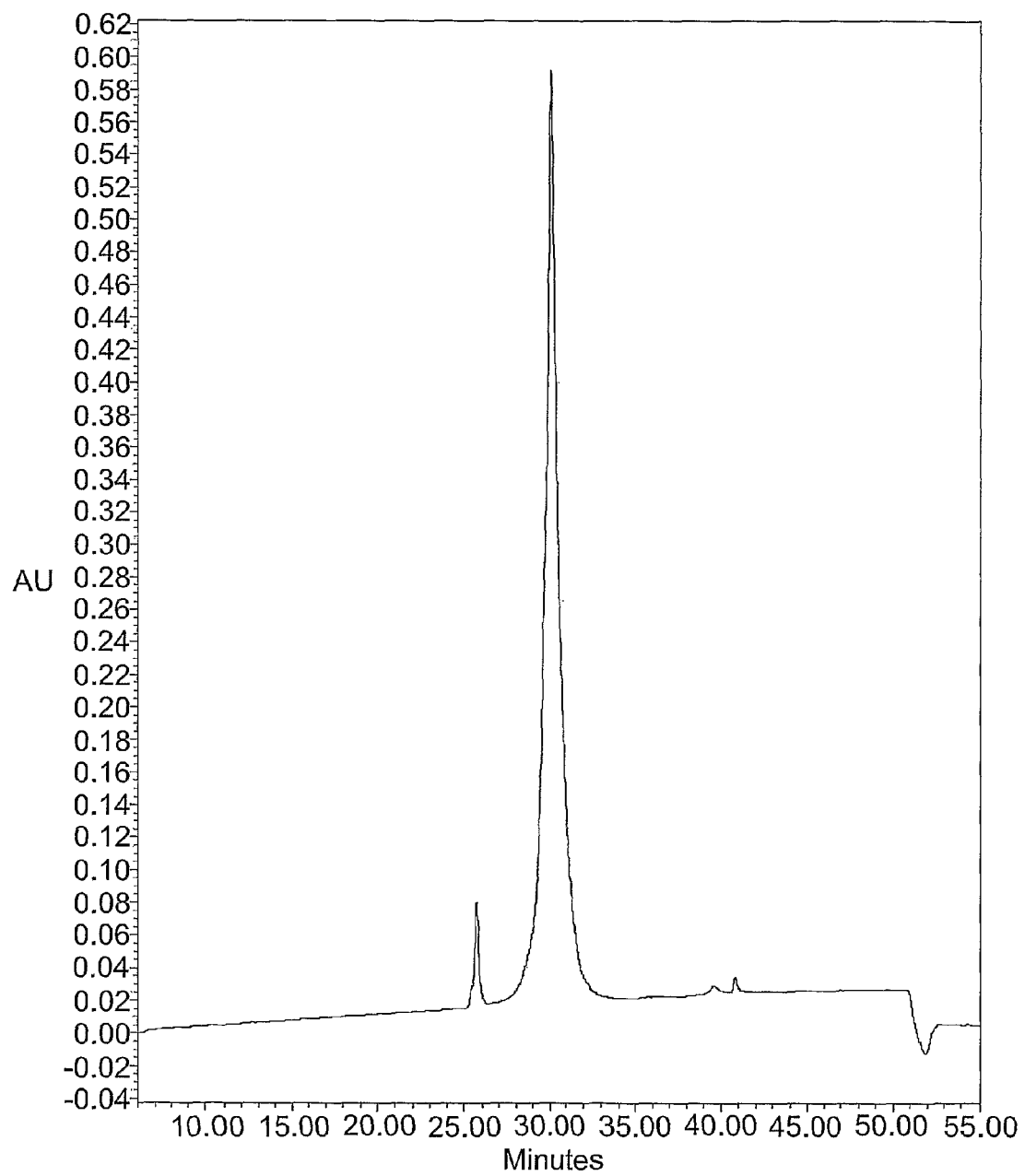
Figure 1C:
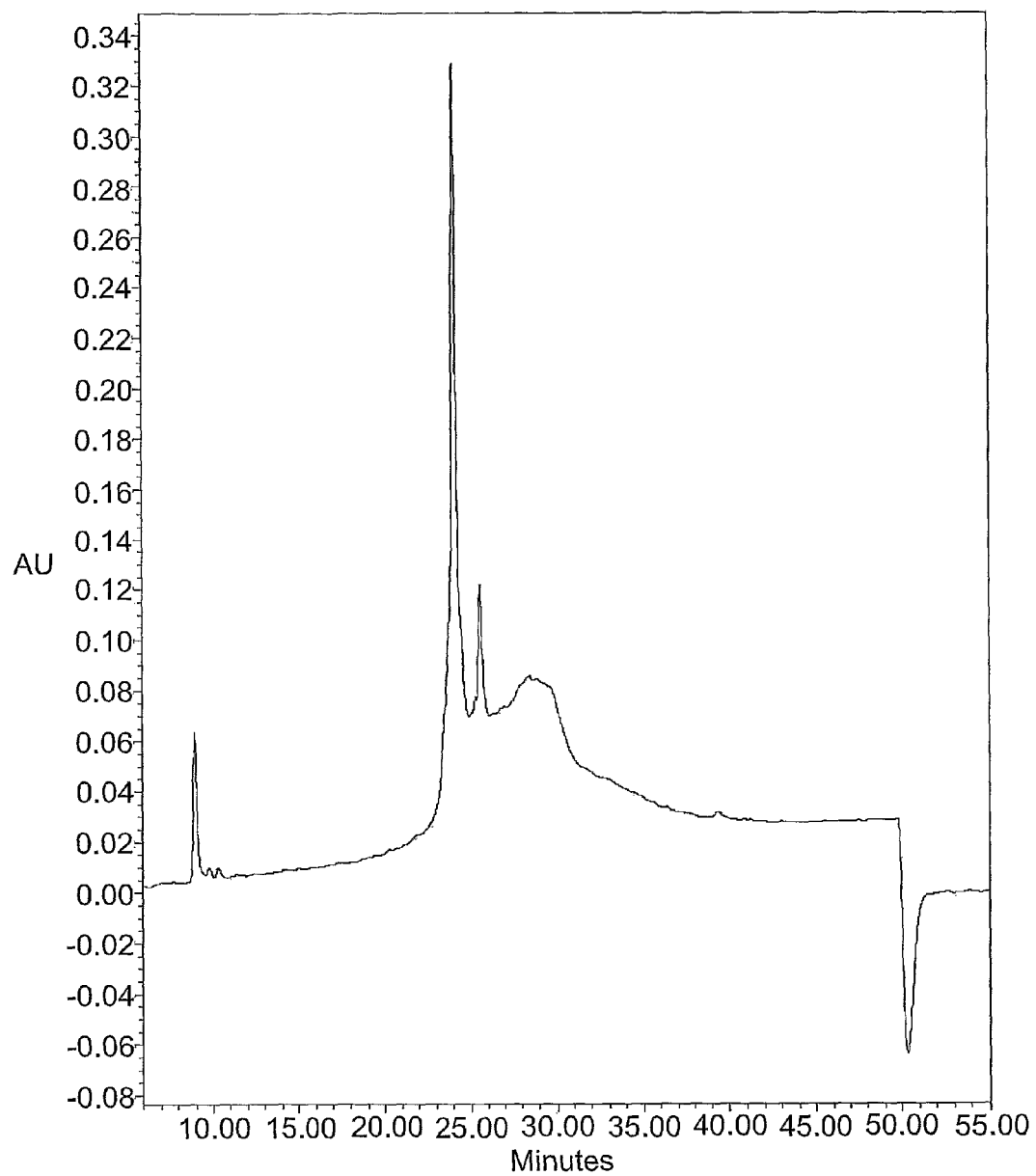
Figure 1D:
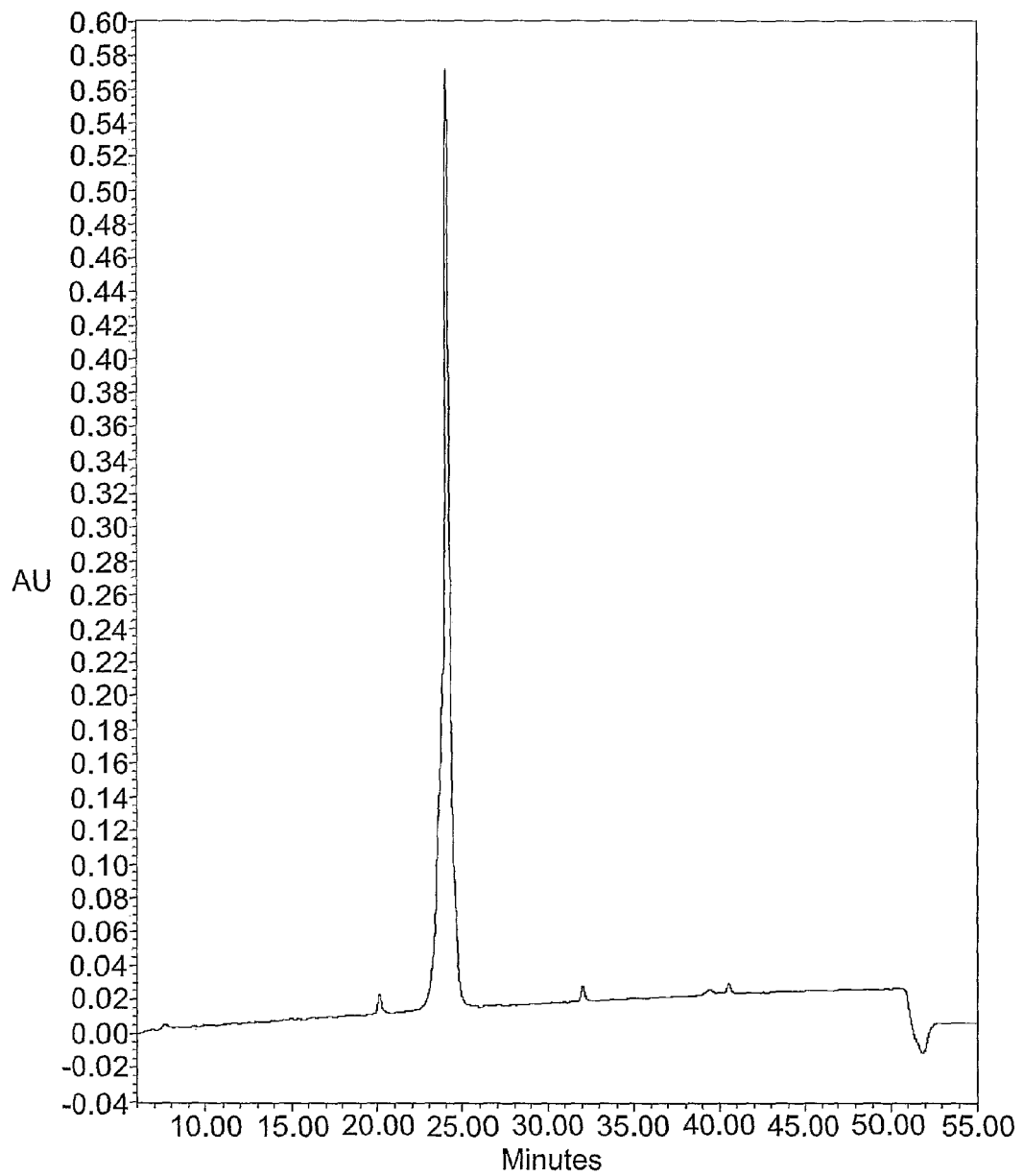

Preparation of chemokines by total chemical synthesis was carried out on a modified ABI 430 peptide synthesizer customized to perform Boc chemistry with in situ neutralization [22]. The synthesis strategy also featured a chemical capping step (to terminate any chains with free amine groups at the end of the coupling step) using acetylglycine at each cycle. After HF cleavage, crude products were analysed by analytical HPLC and MALDI mass spectrometry. After preparative scale purification of the desired product, refolding of proteins and formation of disulphide bridges was carried out according to published procedures [23], and the refolded material was verified by analytical HPLC (shorter retention time) and electrospray mass spectrometry (loss of mass units due to oxidation of cysteine thiol group during disulphide bridge formation). Final products were subjected to preparative scale purification and then lyophilized. Details of the characterisation of intermediate and partially purified material by HPLC for a typical synthesis, of a protein of the invention consisting of SEQ ID NO: 21 fused to the N terminus of SEQ ID NO: 1, are shown in FIG. 1. Results of characterisation of the purified material of said protein by mass spectrometry are provided in the following table:

TABLE 3

Characterisation of purified material by mass spectrometry

| Protein consisting of SEQ ID NO: 21 fused to the N-terminus of SEQ ID NO: 1 | Calculated mass | Observed mass |
| --- | --- | --- |
| Material before refolding | 7976.26 | 7976.76 ± 0.24 |
| Material after refolding | 7922.26 | 7972.68 ± 0.36 |

The analysis of the final product by analytic HPLC is shown in FIG. 1.

Preparation of Polypeptides by Expression in Host Organisms

The polypeptide agents were prepared by expression in host organisms using routine techniques that are known in the art, following procedures described, e.g., in references [13] and [14].

Cell Fusion Assay

This procedure was carried out as described in [5] using the HeLa-P5L [2] and HeLa-Env-ADA [26] cell lines. HeLa-P5L cells were seeded in 96-well plates ($10^4$ cells per well). Twenty-four hours later, medium was removed and replaced with medium containing $10^4$ HeLa-Env-ADA cells per well plus chemokine peptide agents of the present invention. After a further 24 h, cells were washed once in PBS, lysed and assayed for β-galactosidase activity by the addition of the colorigenic substrate CPRG (chlorophenol red-β-D-galactopyranoside). Results were expressed according to the following formula:

100×(mean absorbance[treated]−mean absorbance[no envelope cells])/(mean absorbance[no chemokine]−mean absorbance[no envelope cells]).

Measurements were performed in triplicate for each independent experiment, and IC50 values obtained from dose-inhibition curves fitted using Prism® software (GraphPad). The IC50 value represents the concentration of a peptide agent at which cell fusion was inhibited by 50%, in comparison with a control that had not been exposed to any inhibitory agent.

Viral Replication Assay

Viral replication was assayed as described in references [24] and [25], with the modification that HeLa cells were used starting material and SX22-1 reporter cells were added only after virus expression.

Calcium Flux Assay

Agents were assayed for stimulation of calcium signalling via either CCR5, CCR1 or CCR3 using cells (e.g. Human Embryonic Kidney (HEK) cells) transfected to give stable expression of either CCR5, CCR1 or CCR3, respectively. The procedure was carried out essentially as described in reference [6], using 96-well plates and a FLEXstation fluorimeter (Molecular Devices). Fluorescence measurements were carried out on said cells loaded with Fluo-4 (Molecular Probes) according to the manufacturer's recommendations and maintained at 37° C. Measurements were performed in sextuplicate (n=6) at a single agent concentration (300 nM; a concentration that gives $E_{max}$ for PSC-RANTES and native RANTES).

CCR5 Surface Downmodulation Assay

CHO-CCR5 cells [5] were seeded at 80,000 cells/ml in 96-well plates. The next day, medium was removed and replaced with medium containing chemokines at different concentrations and the cells were incubated for 1 h at 37° C. At the end of this period, medium was removed and the cells were fixed with 4% paraformaldehyde. After two washes with PBS, solutions of either phycoerythrin-conjugated anti-CCR5 antibody (clone 3A9, Pharmingen) or phycoerythrin-conjugated anti-CCR1 antibody (for negative control) in PBS-1% BSA were added to the cells. Plates were left on ice for 1 h, then washed three times with PBS-1% BSA before fluorescence values were determined using a FLEXstation fluorimeter. Results were expressed as % control level of surface CCR5:

100×(mean fluorescence[chemokine added, anti-CCR5]−mean negative control fluorescence[anti-CCR1])/(mean positive control fluorescence[no chemokine added, anti-CCR5]−mean fluorescence[anti-CCR1]).

Each determination was performed in sextuplicate (n=6), and PSC-RANTES was used as a reference chemokine in every experiment.

CCR1 Discrimination Assay

Selectivity for CCR5 over CCR1 was measured in a CCR1 competition binding assay using a radiolabelled natural CCR1 ligand as a tracer. Either MIP-RANTES/CCL5 may, for example, be used as a tracer for this CCR1 Discrimination Assay. The assay was carried out described in as in reference [27].

CCR3 Discrimination Assay

Selectivity for CCR5 over CCR1 was measured in a CCR3 competition binding assay using a radiolabelled natural CCR3 ligand as a tracer. Eotaxin/CCL11 or RANTES/CCL5 may, for example, be used as a tracer for this CCR3 Discrimination Assay. The assay was carried out described in as in reference [28].

EXAMPLES

Example 1

Anti-HIV Potency Measurement by the Cell Fusion Assay

Peptide agents were prepared by chemical synthesis as described under Materials and Methods. The agents were individually evaluated using the Cell Fusion Assay as described under Materials and Methods, and IC50 values were obtained by comparison of the assay result in the presence of the agents with the assay result obtained in the absence of the agents. The IC50 values obtained are listed in Table 4.

In general, low IC50 values, i.e., high anti-HIV potency values, were found for peptide agents that conformed well to the N-terminal consensus signature sequence Q G P [P/L] [L/G] [M/D] X X [Q/L] X or QGP[P or L][L or G or S or M][M or D or S or Q or G]XX[Q or G or L or A or T or S]X, wherein X represents any amino acid and "/" represents "or". Examples of such compounds are those RANTES derivatives consisting of the N-terminal signature sequences SEQ ID NO: 2-69 fused to positions 10-68 of the native RANTES sequence (SEQ. ID. NO: 1)

TABLE 4

Characterisation of peptide agents of the invention

| Signature sequence SEQ ID NO: | anti-HIV potency (IC50, nM) by cell fusion assay | anti-HIV potency (IC50, nM) by viral replication assay | CCR5 signalling (%) [1] | CCR5 sequestration (%) [2] |
|---|---|---|---|---|
| 2 | 0.02 | 0.194 | 1.4 | 5 |
| 3 | 0.02 |  | <5 | 3 |
| 4 | 0.02 | 0.380 | 4.6 | 3 |
| 5 | 0.02 | 0.576 | 5.3 | 0 |
| 6 | 0.02 | 0289 | 1.4 | 3 |
| 7 | 0.02 | 0.179 | 0.7 | 10 |
| 8 | 0.03 | 0.278 | 2.5 | 0 |
| 9 | 0.03 | 0.187 | 4.8 | 2 |
| 10 | 0.03 | 0.403 | 2.3 | 0 |
| 11 | 0.03 |  | 1.6 | 9 |
| 12 | 0.03 | 0.204 | 4.1 | 4 |
| 13 | 0.07 |  | <5 | 9 |
| 14 | 0.13 |  | 1.4 | 8 |
| 15 | 0.65 |  | 2.4 | 2 |
| 16 | 0.02 | 0.091 | 96.3 | 70 |
| 17 | 0.02 | 129 | 87.7 | 70 |
| 18 | 0.08 |  | 90.1 | 69 |
| 19 | 0.28 |  | 85.1 | 66 |
| 20 | 0.66 |  | 95.6 | 71 |
| 21 | 0.54 |  | 14.2 | 54 |
| 22 | 0.02 | 0.470 | 2.4 | 12 |
| 23 | 0.03 | 0.625 | 5.3 | 35 |
| 24 | 0.03 | 0.174 | 2.4 | 35 |
| 25 | 0.03 |  | 0.0 | 13 |
| 26 | 0.58 |  | 9.4 | 41 |
| 27 | 0.03 |  | 14.6 | 40 |
| 28 | 0.03 | 0.213 | 45.0 | 59 |
| 29 | 0.39 |  | 22.6 | 36 |
| 30 | 0.01 |  | 4.1 | 4 |
| 31 | 0.02 |  | 3.6 | 6 |
| 32 | 0.03 |  | 6.0 | 5 |
| 33 | 0.03 |  | 0.2 | 0 |
| 34 | 0.03 |  | 5.1 | 8 |
| 35 | 0.05 |  | 4.9 | 5 |
| 36 | 0.05 |  | 5.1 | 7 |
| 37 | 0.09 |  | 0.7 | 5 |
| 38 | 0.10 |  | 0.3 | 3 |
| 39 | 0.10 |  | 1.7 | 5 |

TABLE 4-continued

Characterisation of peptide agents of the invention

| Signature sequence SEQ ID NO: | anti-HIV potency (IC50, nM) by cell fusion assay | anti-HIV potency (IC50, nM) by viral replication assay | CCR5 signalling (%) [1] | CCR5 sequestration (%) [2] |
|---|---|---|---|---|
| 40 | 0.11 | | 0 | 6 |
| 41 | 0.12 | | 0 | 9 |
| 42 | 0.16 | | 0.2 | 0 |
| 43 | 0.29 | | 0.3 | 4 |
| 44 | 0.02 | | 68.5 | 60 |
| 45 | 0.02 | | 77.4 | 62 |
| 46 | 0.40 | | 97.6 | 72 |
| 47 | 0.44 | | 96.9 | 78 |
| 48 | 0.64 | | 100.5 | 78 |
| 49 | 0.74 | | 97.2 | 77 |
| 50 | 0.02 | | 7.6 | 11 |
| 51 | 0.02 | | 5.0 | 12 |
| 52 | 0.02 | | 8.3 | 11 |
| 53 | 0.02 | | 5.1 | 16 |
| 54 | 0.06 | | 2.1 | 12 |
| 55 | 0.07 | | 7.3 | 33 |
| 56 | 0.15 | | 7.5 | 15 |
| 57 | 0.16 | | 4.9 | 18 |
| 58 | 0.23 | | 0.7 | 25 |
| 59 | 0.23 | | 6.0 | 15 |
| 60 | 0.02 | | 11.8 | 8 |
| 61 | 0.02 | | 12.7 | 7 |
| 62 | 0.03 | | 29.6 | 45 |
| 63 | 0.03 | | 42.7 | 50 |
| 64 | 0.04 | | 17.2 | 28 |
| 65 | 0.04 | | 11.5 | 30 |
| 66 | 0.07 | | 33.4 | 42 |
| 67 | 0.12 | | 10.3 | 15 |
| 68 | 0.17 | | 10.6 | 24 |
| 69 | 0.22 | | 20.1 | 38 |

[1] % signalling is expressed as % of the maximal response ($E_{max}$) elicited by PSC-RANTES, when tested at a concentration of 300 nM in the Calcium Flux signalling assay as described under Materials and Methods.
[2] Sequestration % is expressed as the amount of sequestration with respect to the control level of surface CCR5 molecules, when tested in the CCR5 Surface Downmodulation/receptor sequestration assay as described under Materials and Methods.

Example 2

Anti-HIV Potency Measurement by the Viral Replication Assay

Peptide agents of the invention were prepared by chemical synthesis as described under Materials and Methods. The agents were individually evaluated using the Viral Replication Assay as described under Materials and Methods, and IC50 values were obtained by comparison of the assay result in the presence of the agents with the assay result obtained in the absence of the agents. The IC50 values obtained are listed in Table 4.

In general, low IC50 values, i.e., high anti-HIV potency values, were found for peptide agents that conformed well to the N-terminal consensus signature sequence Q G P [P/L] [L/G] [M/D] X X [Q/L] X wherein X represents any amino acid and "/" represents "or". Examples of such compounds are those RANTES derivatives consisting of the N-terminal signature sequences SEQ ID NO: 2-29 fused to positions 10-68 of the native RANTES sequence (SEQ. ID. NO: 1).

Example 3

Measurement of Cellular Signalling by the Calcium Flux Assay

Peptide agents prepared by chemical synthesis as described under Materials and Methods were evaluated using the Calcium Flux Assay as described under Materials and Methods. The "signalling" values obtained using said assay for individual peptide agents of the present invention are listed in Table 4.

In general, low signalling values of, for example, at most 6% or 10% were found for peptide agents that conformed well to the N-terminal consensus signature sequence Q G P P L M [S/G] [L/F/T] Q [S/V] wherein "/" represents "or". Examples of such compounds are those RANTES derivatives consisting of the N-terminal signature sequences SEQ ID NO: 22, SEQ ID NO: 23, SEQ ID NO: 24, or SEQ ID NO: 25 fused to positions 10-68 of the native RANTES sequence (SEQ. ID. NO: 1). However, RANTES derivatives of the present invention with other signature sequences, such as SEQ ID NO: 27 and SEQ ID NO: 21 also displayed low signalling values of 20% or less, the peptide agent carrying the signature sequence SEQ ID NO: 29 achieved a low signalling value of 30% or less, and the peptide agent carrying the signature sequence SEQ ID NO: 28 achieved a signalling value of below 46%. Overall, low signalling values were observed for peptide agents that conformed to the N-terminal consensus signature sequence QGPP[G/L]M[/Q]XX[Q/S][S/V], or QGPP[G/L][M/Q][S/G/W/A/T][L/F/T/S/G/Y][Q/S][S/V], for example, including RANTES derivatives having the N-terminal signature sequences SEQ ID NO: 50, SEQ ID NO: 51, SEQ ID NO: 52, SEQ ID NO: 53, SEQ ID NO: 54, or SEQ ID NO: 55.

Example 4

Assay of Receptor Sequestration by the CCR5 Surface Downmodulation Assay

Peptide agents prepared by chemical synthesis as described under Materials and Methods were evaluated using the CCR5 Surface Downmodulation Assay as described under Materials and Methods. The "CCR5 sequestration" values obtained using said assay for individual peptide agents of the present invention are listed in Table 4. CCR5 sequestration values obtained in the equivalent tests from prior art documents are listed in Table 5.

In general, high CCR5 sequestration values of, for example, at least 60% or 65% or more were, found for peptide agents that conformed well to the N-terminal consensus signature Q G P P G D [T/I] V L [W/A], wherein "/" represents "or". Examples of such compounds are those RANTES derivatives consisting of the N-terminal signature sequences SEQ ID NO: 16 or SEQ ID NO: 17 fused to positions 10-68 of the native RANTES sequence (SEQ. ID. NO: 1). However, RANTES derivatives of the present invention with other signature sequences, such as SEQ ID NO: 18, SEQ ID NO: 19, SEQ ID NO: 20 were also characterised by high CCR5 sequestration activity of, e.g. 60% or 65%, or more. Moreover, the RANTES derivative peptide agents with the signature sequences SEQ ID NO: 21 and SEQ ID NO: 28 were also characterised by high CCR5 sequestration activity, i.e. of at least 50%, or at least 54, 55 or 59%. Overall, high CCR5 sequestration values were observed for peptide agents that conformed to the N-terminal consensus signature sequence QGP[P/L][L/G/S][D/S/G/Q]XX[L/A/T/Q][W/A/V], or QGP[P/L][L/G/S][D/S/G/Q][T/I/S/W/Q][V/L/A/S/G][L/A/T/Q][W/A/V], for example, including RANTES derivatives having the N-terminal signature sequences SEQ ID NO: 44, SEQ ID NO: 45, SEQ ID NO: 46, SEQ ID NO: 47, SEQ ID NO: 48, SEQ ID NO: 49.

Example 5

Comparative Example

Prior art RANTES derivatives as listed in Table 5 were evaluated using assays as described for the agents of the invention in Example 1 to Example 4. The results obtained in these assays with the prior art RANTES derivatives are listed in Table 5.

TABLE 5

Characterisation of selected prior art cytokine derivatives

| Agent name | anti-HIV potency (IC50, nM) by cell fusion assay | anti-HIV potency (IC50, nM) by viral replication assay | CCR5 signalling (%) [1] | CCR5 sequestration (%) [2] |
|---|---|---|---|---|
| Met-RANTES [3] | 75.14 | | 15.0 | 26 |
| AOP-RANTES [4] | 1.12 | | 80.7 | 71 |
| NNY-RANTES [5] | 0.29 | | 84.5 | 77 |
| PSC-RANTES [6] | 0.02 | 0.281 | 100.0 | 75 |
| P1 [7] | 6.59 | | 0.0 | 5 |
| P2 [7] | 1.61 | | 93.8 | 68 |

[1] % signalling is expressed as % of the maximal response ($E_{max}$) elicited by PSC-RANTES, when tested at a concentration of 300 nM in the Calcium Flux signalling assay as described under Materials and Methods.
[2] Sequestration % is expressed as the amount of sequestration with respect to the control level of surface CCR5 molecules, when tested in the CCR5 Surface Downmodulation/receptor sequestration assay as described under Materials and Methods.
[3] compound reported in ref. [13]
[4] compound reported in ref. [2]
[5] compound reported in ref. [3]
[6] compound reported in ref. [5]
[7] compound reported in ref. [6]

Example 6

Testing In Vitro Efficacy of New Molecules Against Worldwide HIV Clades

The molecules are tested against representative R5 strains from around the world.

In brief, primary HIV isolates obtained from different field sites around the world and made available through reagent repositories are tested for their sensitivity to inhibition in replication assays using human primary cells.

The procedure may be carried out as described in reference [29], or as follows:

Cell cultures. PBMC are purified from blood from different HIV-negative human donors by Ficoll-Paque gradient centrifugation. Purified PBMC are resuspended in RPMI (Mediatech, Inc., Herndon, Pa.) medium supplemented with 10% foetal bovine serum (FBS; Life Technologies, Inc., Rockville, Md.), 100 U of penicillin and 100 μg of streptomycin (pen/strep; Mediatech, Inc.) per ml, 1 ng of recombinant human interleukin-2 (IL-2; Life Technologies, Inc.) per ml, and 1 U of phytohemagglutinin (PHA; Life Technologies, Inc.) per ml.

Viruses. The following NSI R5 HIV-1 strains are obtained from the AIDS Research and Reagent Program: A-92RW009, A-92RW008, A-93UG075, B-92BR021, B-92TH026, B-BaL, C-92BR025, C-93IN101, D-94UG108, E/A-92TH022, E-92TH001, B/F-93BR019, F-93BR029, G-92NG083-JV1083, and G-92NG003-G3. Two SI X4 strains (HXB2 and F-93BR020) are also obtained from the AIDS Reagent Program for use as controls. For most of the strains listed above, the letter before the dash indicates the subtype of the viral envelope and is followed by the year of isolation, country of origin, and strain number, e.g., A-92RW009 is a clade A HIV-1 strain isolated in Rwanda in 1992. All of these viruses are propagated in PBMC cultures until high virus titers (as determined by reverse transcriptase [RT] activity) are obtained in culture supernatants. The 50% tissue culture infective dose values are then calculated for each virus using the Reed-Muench technique [30].

Replication assays. PHA/IL-2-treated PBMC are added to 96-well plates ($2 \times 10^5$ cells/well) containing serially diluted inhibitors. The appropriate HIV-1 isolate in complete RPMI medium (approximately 0.1 multiplicity of infection [MOI]) is then added. Triplicate experiments are performed with all NSI R5 HIV-1 isolates. On day 3 post-infection, each plate is centrifuged for 5 min at 1,200×g in a swinging-bucket centrifuge. An aliquot (150 μl) of cell-free supernatant is then removed from each well and replaced with 150 μl of complete RPMI medium containing the appropriate concentrations of inhibitor. On days 5, 10, and 15 post-infection, each plate is centrifuged again for 5 min, and cell-free supernatant samples (25 μl) are removed and stored at −70° C. for subsequent analysis. Cultures are discarded on day 15.

Virus production in the presence of inhibitors is measured in cell-free supernatants using RT assays as described previously [31].

Example 7

Demonstration of In Vivo Efficacy of CCR5 Inhibitors in a Non-Human Primate Model of Vaginal HIV Transmission The macaque model for HIV prevention described below is used to demonstrate the in vivo efficacy of the molecules of the invention.

In brief, groups of progesterone-treated adult female rhesus macaques are pre-treated with 4 mL of either PBS or solutions of inhibitors in PBS. Fifteen minutes later, animals are challenged with 300 $TCID_{50}$ of SHIV SF162 and monitored for up to 24 weeks for the development of plasma viremia [32].

The procedure may be carried out as described in reference [33], or as follows:

Normal cycling, adult female rhesus macaques (*Macacca mulatta*) ranging from 5 to 12 years of age are used. All studies adhere to the Guide for the Care and Use of Laboratory Animals, prepared by the National Research Council, National Institutes of Health, and with the Guidelines of the Tulane National Primate Research Center Institutional Animal Care and Use Committee. All key personnel (animal handlers, treaters and laboratory technicians engaged in preparation of viral inocula and in virologic analyses) are blinded as to treatment assignment.

Animals are treated with a single 30 mg intramuscular injection of depo-medroxyprogesterone acetate (Depo-Provera®). After 30-33 days they are sedated with telazol, placed in ventral recumbency with hips elevated, and 4 ml of inhibitor solution in PBS, or PBS alone is introduced without trauma into the vaginal vault using a pliable French catheter. This volume provides the most effective coverage of the vaginal vault walls without undue leakage. The animals are challenged 15 min later with 300 $TCID_{50}$ of SHIV SF162 obtained from the NIH AIDS Research and Reference Reagent Program in 1 ml of RPMI 1640 medium. Blood is collected in EDTA tubes every week post-challenge. Plasma viral levels are determined by quantifying SIV gag RNA using a real-time RT-PCR assay, as described previously [32]. The assay has a sensitivity threshold of 60 RNA copies/ml with an inter-assay coefficient of variation of <25%. Infection-free status is defined as a consistently undetectable plasma viremia for all of the analyses. Seroconversion is monitored by Western Blot using the Zeptometrix SIV Western Blot kit (Zeptometrix, Buffalo N.Y.).

REFERENCES

1. Samson M, Libert F, Doranz B J, Rucker J, Liesnard C, Farber C M, Saragosti S, Lapoumeroulie C, Cognaux J, Forceille C, Muyldermans G, Verhofstede C, Burtonboy G, Georges M, Imai T, Rana S, Yi Y, Smyth R J, Collman R G, Doms R W, Vassart G, Parmentier M. Resistance to HIV-1 infection in caucasian individuals bearing mutant alleles of the CCR-5 chemokine receptor gene. Nature. 1996 Aug. 22; 382(6593):722-5.
2. Simmons G, Clapham P R, Picard L, Offord R E, Rosenkilde M M, Schwartz T W, Buser R, Wells T N, Proudfoot A E. Potent inhibition of HIV-1 infectivity in macrophages and lymphocytes by a novel CCR5 antagonist. Science. 1997 Apr. 11; 276(5310):276-9.
3. Mosier D E, Picchio G R, Gulizia R J, Sabbe R, Poignard P, Picard L, Offord R E, Thompson D A, Wilken J. Highly potent RANTES analogues either prevent CCR5-using human immunodeficiency virus type I infection in vivo or rapidly select for CXCR4-using variants. J. Virol. 1999 May; 73(5):3544-50.
4. Sabbe R, Picchio G R, Pastore C, Chaloin O, Hartley O, Offord R, Mosier D E. Donor- and ligand-dependent differences in C—C chemokine receptor 5 reexpression. J. Virol. 2001 January; 75(2):661-71.
5. Hartley O, Gaertner H, Wilken J, Thompson D, Fish R, Ramos A, Pastore C, Dufour B, Cerini F, Melotti A, Heveker N, Picard L, Alizon M, Mosier D, Kent S, Offord R. Medicinal chemistry applied to a synthetic protein: development of highly potent HIV entry inhibitors. Proc Natl Acad Sci USA. 2004 Nov. 23; 101(47):16460-5. Epub 2004 Nov. 15.
6. Hartley O, Dorgham K, Perez-Bercoff D, Cerini F, Heimann A, Gaertner H, Offord R E, Pancino G, Debre P, Gorochov G. Human immunodeficiency virus type 1 entry inhibitors selected on living cells from a library of phage chemokines. J. Virol. 2003 June; 77(12):6637-44.
7. WO 03/022884.
8. Lloyd-Williams P, Albericio F, Giralt E. Chemical Approaches to the Synthesis of Peptides and Proteins. CRC Press. 1997. ISBN 0849391423.
9. Benoiton N L. Chemistry of Peptide Synthesis. CRC Press. 2005. ISBN 1574444549.
10. Chan W, White P. Fmoc Solid Phase Peptide Synthesis. Oxford University Press. 2000. ISBN: 0199637245.
11. Kullmann W. Enzymatic Peptide Synthesis. CRC Press. 1987. ISBN 0849368413.
12. Ibba M. Strategies for in vitro and in vivo translation with non-natural amino acids. Biotechnol Genet Eng Rev. 1996; 13:197-216.
13. Proudfoot, A. E., Power, C. A., Hoogewerf, A. J., Montjovent, M. O., Borlat, F., Offord, R. E., and Wells, T. N. J Biol. Chem. 1996; 271: 2599-2603.
14. Sambrook J, Russell D W. Molecular Cloning: A Laboratory Manual. Cold Spring Harbor Laboratory Press; 3rd edition (Jan. 15, 2001). ISBN 087969576.
15. Rao S, Hu S, McHugh L, Lueders K, Henry K, Zhao Q, Fekete R A, Kar S, Adhya S, Hamer D H. Toward a live microbial microbicide for HIV: commensal bacteria secreting an HIV fusion inhibitor peptide. Proc Natl Acad Sci USA. 2005 Aug. 23; 102(34):11993-8. Epub 2005 Jul. 22.
16. Chang T L, Chang C H, Simpson D A, Xu Q, Martin P K, Lagenaur L A, Schoolnik G K, Ho D D, Hillier S L, Holodniy M, Lewicki J A, Lee P P. Inhibition of HIV infectivity by a natural human isolate of Lactobacillus jensenii engineered to express functional two-domain CD4. Proc Natl Acad Sci USA. 2003 Sep. 30; 100(20):11672-7. Epub 2003 Sep. 12.
17. Lagenaur L A, Berger E A. An anti-HIV microbicide comes alive. Proc Natl Acad Sci USA. 2005 Aug. 30; 102(35):12294-5. Epub 2005 Aug. 23.
18. FDA (US Food and Drug Administration) web page. Inactive Ingredient Guide. 1996. http://www.fda.gov/cder/drug/iig/default.htm
19. Ash M and Ash I. Handbook of Pharmaceutical Additives. Synapse Information Resources. 2nd Edition. 2002. ISBN 1890595349
20. Gennaro A R (ed.). Remington: The Science and Practice of Pharmacy. Lippincott Williams & Wilkins. 21st edition. Jul. 3, 2005. ISBN 0781763789.
21. Hardman J G, Limbird L E, Alfred G. Gilman A G. Goodman & Gilman's The Pharmacological Basis of Therapeutics. McGraw-Hill; 10th edition. Aug. 13, 2001. ISBN 0071354697.
22. Schnolzer M, Alewood P, Jones A, Alewood D, Kent S B. In situ neutralization in Boc-chemistry solid phase peptide synthesis. Rapid, high yield assembly of difficult sequences. Int J Pept Protein Res. 1992 September-October; 40(3-4): 180-93.
23. Wilken J, Hoover D, Thompson D A, Barlow P N, McSparron H, Picard L, Wlodawer A, Lubkowski J, Kent S B. Total chemical synthesis and high-resolution crystal structure of the potent anti-HIV protein AOP-RANTES. Chem. Biol. 1999 January; 6(1):43-51.
24. Klimkait T, Stauffer F, Lupo E, Sonderegger-Rubli C. Dissecting the mode of action of various HIV-inhibitor classes in a stable cellular system. Arch Virol. 1998; 143 (11):2109-31.
25. Sune C, Brennan L, Stover D R, Klimkait T. Effect of polymorphisms on the replicative capacity of protease inhibitor-resistant HIV-1 variants under drug pressure. Clin Microbiol Infect. 2004 February; 10(2): 119-26.
26. Pleskoff O, Treboute C, Brelot A, Heveker N, Seman M, Alizon M. Identification of a chemokine receptor encoded by human cytomegalovirus as a cofactor for HIV-1 entry. Science. 1997 Jun. 20; 276(5320):1874-8.
27. Neote, K., DiGregorio, D., Mak, J. Y., Horuk, R., and Schall, T. J. Cell. 1993; 72: 415-425
28. Daugherty, B. L., Siciliano, S. J., DeMartino, J. A., Malkowitz, L., Sirotina, A., and Springer, M. S. J Exp Med. 1996; 183: 2349-2354
29. Torre V S, Marozsan A J, Albright J L, Collins K R, Hartley O, Offord R E, Quinones-Mateu M E, Arts E J. 2000. Variable sensitivity of CCR5-tropic human immunodeficiency virus type 1 isolates to inhibition by RANTES analogs. J Virol 74: 4868-76
30. Coligan, J. E., A. M. Kruisbeek, D. H. Margulies, E. M. Shevach, W. Strober, and R. Coico. 1999. Detection and analysis of HIV; isolation and quantitation of HIV in peripheral blood, alternate protocol: assessment of HIV titer using the Reed-Muench accumulative method, p. 12.2.5. In Current protocols in immunology, CD-ROM version. John Wiley & Sons, Inc., New York, N.Y.

31. Coligan, J. E., A. M. Kruisbeek, D. H. Margulies, E. M. Shevach, W. Strober, and R. Coico. 1999. Detection and analysis of HIV; detection assays for HIV proteins, basic protocol: assay for HIV reverse transcriptase activity, p. 12.5.8. In *Current protocols in immunology*, CD-ROM version. John Wiley & Sons, Inc., New York, N.Y.

32. Lifson J D, Rossio J L, Piatak M, Jr., Parks T, Li L, Kiser R, Coalter V, Fisher B, Flynn B M, Czajak S, Hirsch V M, Reimann K A, Schmitz J E, Ghrayeb J, Bischofberger N, Nowak M A, Desrosiers R C, Wodarz D. 2001. Role of CD8(+) lymphocytes in control of simian immunodeficiency virus infection and resistance to rechallenge after transient early antiretroviral treatment. *J Virol* 75: 10187-99

33. Lederman M M, Veazey R S, Offord R, Mosier D E, Dufour J, Mefford M, Piatak M, Jr., Lifson J D, Salkowitz J R, Rodriguez B, Blauvelt A, Hartley O. 2004. Prevention of vaginal SHIV transmission in rhesus macaques through inhibition of CCR5. *Science* 306: 485-7

The invention claimed is:

1. A polypeptide comprising an N-terminal portion and a C-terminal portion, wherein said N-terminal portion comprises the signature sequence QGP[P or L] and the amino acid sequence of said C-terminal portion is at least 70% identical to SEQ ID NO: 1.

2. A polypeptide according to claim 1 wherein the signature sequence is QGP[P or L] [L or G or S or M] [M or D or S or Q or G].

3. A polypeptide according to claim 1 wherein the signature sequence is QGP[P or L][L or G][M or D or S].

4. A polypeptide according to claim 1 wherein the signature sequence is QGP[P or L][L or G or S or M][M or D or S or Q or G]XX[Q or G or L or A or T or S]X, wherein X denotes any natural or modified amino acid.

5. A polypeptide according to claim 1 wherein the signature sequence is QGP[P or L][L or G][M or D or S]XX[Q or G or L]X, wherein X denotes any natural or modified amino acid.

6. A polypeptide according to claim 1 wherein the signature sequence is QGP[P or L]LM or QGPPG[D or S].

7. A polypeptide according to claim 1 wherein the signature sequence is QGPPLM or QGPPGD.

8. A polypeptide according to claim 1 wherein the signature sequence is QGP[P or L][L or M][M or Q][A or W or G or Q or N]X[Q or G or L][S or V or T or G], wherein X denotes any natural or modified amino acid.

9. A polypeptide according to claim 1 wherein the signature sequence is QGP[P or L][L or M][M or Q][A or W or G or Q or N][L or T or M or S or G or Q or R or Y][Q or G or L][S or V or T or G].

10. A polypeptide according to claim 1 wherein the signature sequence is QGP[P or L]LM[A or W][L or T or M][Q or G][S or V or T or G].

11. A polypeptide according to claim 1 wherein the signature sequence is QGPPLM[A or W][L or T or M][Q or G][S or V or T or G].

12. A polypeptide according to claim 1 wherein the signature sequence is QGP[P or L][L or G or S][D or S or G or Q]XX[L or A or T or Q][W or A or V], wherein X denotes any natural or modified amino acid.

13. A polypeptide according to claim 1 wherein the signature sequence is QGP[P or L][L or G or S][D or S or G or Q][T or I or S or W or Q][V or L or A or S or G][L or A or T or Q][W or A or V].

14. A polypeptide according to claim 1 wherein the signature sequence is QGPPG[D or S][T or I]VL[W or A].

15. A polypeptide according to claim 1 wherein the signature sequence is QGPPGD[T or I]VL[W or A].

16. A polypeptide according to claim 1 wherein the signature sequence is QGPP[G or L][M or Q]XX[Q or S][S or V], wherein X denotes any natural or modified amino acid.

17. A polypeptide according to claim 1 wherein the signature sequence is QGPP[G or L][M or Q][S or G or W or A or T][L or F or T or S or G or Y][Q or S][S or V].

18. A polypeptide according to claim 1 wherein the signature sequence is QGPPLM[S or G][L or F or T]Q[S or V].

19. A polypeptide according to claim 1 wherein the signature sequence is selected from the group QGPPLMALQS (SEQ ID NO: 2), QGPPLMWMQV (SEQ ID NO: 3), QGPPLMWLQV (SEQ ID NO: 4), QGPPLMWTQS (SEQ ID NO: 5), QGPPLMWLQT (SEQ ID NO: 6), QGPPLMWTQV (SEQ ID NO: 7), QGPPLMWMQS (SEQ ID NO: 8), QGPPLMATQS (SEQ ID NO: 9), QGPPLMWLQS (SEQ ID NO: 10), QGPPLMALQV (SEQ ID NO: 11), QGPPLMWLGG (SEQ ID NO: 12), QGPPLMWRGS (SEQ ID NO: 13), QGPLLMWLQV (SEQ ID NO: 14), QGPPLMQTTP (SEQ ID NO: 15), QGPPLSWLQV (SEQ ID NO: 30), QGPPLSWLQS (SEQ ID NO: 31), QGPPGQWSQV (SEQ ID NO: 32), QGPPMMAGLS (SEQ ID NO: 33), QGPPLSWQQS (SEQ ID NO: 34), QGPPGMWSQS (SEQ ID NO: 35), QGPPLQWRQS (SEQ ID NO: 36), QGPPLMGTQS (SEQ ID NO: 37), QGPPLMQLQV (SEQ ID NO: 38), QGPPLSWSQV (SEQ ID NO: 39), QGPPMSWSQS (SEQ ID NO: 40), QGPPLMNLQV (SEQ ID NO: 41), QGPPMSAYQV (SEQ ID NO: 42) and QGPPMQGGLS (SEQ ID NO: 43).

20. A polypeptide according to claim 1 wherein the signature sequence is selected from the group QGPPLMALQS (SEQ ID NO: 2), QGPPLMWMQV (SEQ ID NO: 3), QGPPLMWLQV (SEQ ID NO: 4), QGPPLMWTQS (SEQ ID NO: 5), QGPPLMWLQT (SEQ ID NO: 6), QGPPLMWTQV (SEQ ID NO: 7), QGPPLMWMQS (SEQ ID NO: 8), QGPPLMATQS (SEQ ID NO: 9), QGPPLMWLQS (SEQ ID NO: 10), QGPPLMALQV (SEQ ID NO: 11), QGPPLMWLGG (SEQ ID NO: 12), QGPPLMWRGS (SEQ ID NO: 13), QGPLLMWLQV (SEQ ID NO: 14) and QGPPLMQTTP (SEQ ID NO: 15).

21. A polypeptide according to claim 1 wherein the signature sequence is selected from the group QGPPGDTVLW (SEQ ID NO: 16), QGPPGDIVLA (SEQ ID NO: 17), QGPPGSYDYS (SEQ ID NO: 18), QGPPGDGGSV (SEQ ID NO: 19), QGPLSGQSTP (SEQ ID NO: 20), QGPPGDWLQV (SEQ ID NO: 21), QGPPLMSLAV (SEQ ID NO: 44), QGPPLMSLTV (SEQ ID NO: 45), QGPLSGWAQV (SEQ ID NO: 46), QGPLSQSSQV (SEQ ID NO: 47), QGPLSSQSQV (SEQ ID NO: 48) and QGPLGQQGQV (SEQ ID NO: 49).

22. A polypeptide according to claim 1 wherein the signature sequence is selected from the group QGPPGDTVLW (SEQ ID NO: 16), QGPPGDIVLA (SEQ ID NO: 17), QGPPGSYDYS (SEQ ID NO: 18), QGPPGDGGSV (SEQ ID NO: 19), QGPLSGQSTP (SEQ ID NO: 20) and QGPPGDWLQV (SEQ ID NO: 21).

23. A polypeptide according claim 1 wherein the signature sequence is selected from the group QGPPLMSFQS (SEQ ID NO: 22), QGPPLMSTQS (SEQ ID NO: 23), QGPPLMSLQV (SEQ ID NO: 24), QGPPLMGLQV (SEQ ID NO: 25), QGPLSGWLQV (SEQ ID NO: 26), QGPPLQWFQV (SEQ ID NO: 50), QGPPLQWTQV (SEQ ID NO: 51), QGPPLMALSV (SEQ ID NO: 52), QGPPLMWSQV (SEQ ID NO: 53), QGPPGQWGQV (SEQ ID NO: 54), QGPPGSWSQV (SEQ ID NO: 55), QGPPLMSSQS (SEQ ID NO: 56), QGPPLMGLSV (SEQ ID NO: 57), QGPPLMTLQV (SEQ ID NO: 58) and QGPPGQWYQS (SEQ ID NO: 59).

24. A polypeptide according claim 1 wherein the signature sequence is selected from the group QGPPLMSFQS (SEQ ID NO: 22), QGPPLMSTQS (SEQ ID NO: 23), QGPPLMSLQV (SEQ ID NO: 24), QGPPLMGLQV (SEQ ID NO: 25), and QGPLSGWLQV (SEQ ID NO: 26).

25. A polypeptide according to claim 1 wherein the signature sequence is selected from the group QGPPLMSVLA (SEQ ID NO: 27), QGPPGSWSSV (SEQ ID NO: 28), QGPPLGSMGP (SEQ ID NO: 29), QGPPLQWMQA (SEQ ID NO: 60), QGPPLQWMQV (SEQ ID NO: 61), QGPPLMSTQV (SEQ ID NO: 62), QGPPLMSLSV (SEQ ID NO: 63), QGPPLMSLQS (SEQ ID NO: 64), QGPPLMSLQA (SEQ ID NO: 65), QGPPLMSVQS (SEQ ID NO: 66), QGPPLMSAQS (SEQ ID NO: 67), QGPPLMSGQS (SEQ ID NO: 68) and QGPPLMSGQV (SEQ ID NO: 69).

26. A polypeptide according to claim 1 wherein the signature sequence is selected from the group QGPPLMSVLA (SEQ ID NO: 27), QGPPGSWSSV (SEQ ID NO: 28) and QGPPLGSMGP (SEQ ID NO: 29).

27. A polypeptide according to claim 1, wherein the N-terminal portion consists of no more than 15 amino acids.

28. A polypeptide according to claim 1, wherein the N-terminal portion consists of 10 amino acids.

29. A polypeptide according to claim 1, wherein the C-terminal portion of the polypeptide is identical to SEQ ID NO: 1.

30. A polypeptide according to claim 1, wherein the signature sequence is located at the extreme N-terminus.

31. A vector comprising a nucleic acid molecule encoding the polypeptide of claim 1.

32. A host cell comprising the vector of claim 31.

33. The host cell of claim 32, which is a micro-organism.

34. The host cell of claim 33, wherein the micro-organism belongs to the flora of the human gut or vagina.

35. The host cell of claim 33, wherein the micro-organism belongs to a genus selected from the group consisting of *Bacteroides, Clostridium, Fusobacterium, Eubacterium, Ruminococcus, Peptococcus, Peptostreptococcus, Bifidobacterium, Streptococcus, Escherichia* and *Lactobacillus*.

36. The host cell of claim 33, wherein the micro-organism is selected from the group consisting of *Lactobacillus acidophilus, Lactobacillus crispatus, Lactobacillus gasseri, Lactobacillus iners, Lactobacillus jensenii, Lactobacillus casei, Lactobacillus plantarum, Lactobacillus rhamnosus, Lactobacillus GG, Bifidobacterium bifidum, Bifidobacterium breve, Bifidobacterium infantis, Bifidobacterium longum* and *Streptococcus gordonii*.

37. The host cell of claim 32, which is a human cell.

38. The host cell of claim 32, from which a polypeptide is secreted, said polypeptide comprising an N-terminal portion and a C-terminal portion, wherein said N-terminal portion comprises the signature sequence QGP[P or L] and the amino acid sequence of said C-terminal portion is at least 70% identical to SEQ ID NO: 1.

39. A pharmaceutical composition comprising a polypeptide according to claim 1, or a pharmaceutically acceptable salt thereof, and a pharmaceutically acceptable carrier.

40. A pharmaceutical composition comprising a vector according to claim 31, and a pharmaceutically acceptable carrier.

41. A pharmaceutical composition comprising a host cell according to claim 32, and a pharmaceutically acceptable carrier.

42. A method of treating HIV infection in a subject comprising the administration of a polypeptide as defined in claim 1 or a composition comprising said polypeptide and a pharmaceutically acceptable carrier to the subject.

43. The method according to claim 42 comprising the step of administering a host cell to the subject, wherein said host cell expresses a polypeptide comprising an N-terminal portion and a C-terminal portion, wherein said N-terminal portion comprises the signature sequence QGP[P or L] and the amino acid sequence of said C-terminal portion is at least 70% identical to SEQ ID NO: 1.

44. The method according claim 42, wherein said polypeptide or composition is administered in the form of a suppository, cream, foam, gel or paste.

45. The method according to claim 42 wherein said polypeptide or composition is administered simultaneously separately, or sequentially to a second polypeptide according to claim 1, or a composition comprising said second polypeptide and a pharmaceutically acceptable carrier.

46. A kit comprising a polypeptide as defined in claim 1, or a host cell, wherein said host cell expresses said polypeptide.

* * * * *

UNITED STATES PATENT AND TRADEMARK OFFICE
CERTIFICATE OF CORRECTION

| | | |
|---|---|---|
| PATENT NO. | : 8,686,111 B2 | Page 1 of 1 |
| APPLICATION NO. | : 12/309569 | |
| DATED | : April 1, 2014 | |
| INVENTOR(S) | : Hartley | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1260 days.

Signed and Sealed this
Twenty-first Day of July, 2015

Michelle K. Lee
*Director of the United States Patent and Trademark Office*

UNITED STATES PATENT AND TRADEMARK OFFICE
CERTIFICATE OF CORRECTION

PATENT NO. : 8,686,111 B2
APPLICATION NO. : 12/309569
DATED : April 1, 2014
INVENTOR(S) : Oliver Hartley It is certified that error appears in the above-identified patent and that said Letters Patent is hereby corrected as shown below:

In the Specification

Column 35, SEQ ID NO 25, delete "Gly Gly Pro Pro Leu Met Gly Leu Gln Val" and insert --Gln Gly Pro Pro Leu Met Gly Leu Gln Val--.

Column 35, SEQ ID NO 27, delete "Gly Gly Pro Pro Leu Met Ser Val Leu Ala" and insert --Gln Gly Pro Pro Leu Met Ser Val Leu Ala--.

Signed and Sealed this
Eighth Day of September, 2015

Michelle K. Lee
*Director of the United States Patent and Trademark Office*